US012691150B2

(12) United States Patent
Alvis et al.

(10) Patent No.: US 12,691,150 B2
(45) Date of Patent: Jul. 28, 2026

(54) GROUP B ADENOVIRUS-CONTAINING FORMULATION

(71) Applicant: AKAMIS BIO, INC., Cambridge, MA (US)

(72) Inventors: Simon Alvis, Oxfordshire (GB); Magdalena Kieltyka, Oxfordshire (GB)

(73) Assignee: Akamis Bio, Inc., Cambridge, MA (US)

( * ) Notice: Subject to any disclaimer, the term of this patent is extended or adjusted under 35 U.S.C. 154(b) by 0 days.

(21) Appl. No.: 18/639,598

(22) Filed: Apr. 18, 2024

(65) Prior Publication Data

US 2024/0398879 A1 Dec. 5, 2024

Related U.S. Application Data

(63) Continuation of application No. 16/965,549, filed as application No. PCT/EP2019/052398 on Jan. 31, 2019, now Pat. No. 11,998,580.

(30) Foreign Application Priority Data

Jan. 31, 2018 (GB) ..................................... 1801614

(51) Int. Cl.

| | |
|---|---|
| ***A61K 35/761*** | (2015.01) |
| ***A61K 9/00*** | (2006.01) |
| ***A61K 9/08*** | (2006.01) |
| ***A61K 47/10*** | (2017.01) |
| ***A61K 47/18*** | (2017.01) |
| ***A61K 47/20*** | (2006.01) |
| ***A61K 47/26*** | (2006.01) |

(52) U.S. Cl.

CPC .......... *A61K 35/761* (2013.01); *A61K 9/0019* (2013.01); *A61K 9/08* (2013.01); *A61K 47/10* (2013.01); *A61K 47/183* (2013.01); *A61K 47/20* (2013.01); *A61K 47/26* (2013.01)

(58) Field of Classification Search

None

See application file for complete search history.

(56) References Cited

U.S. PATENT DOCUMENTS

| | | | | |
|---|---|---|---|---|
| 5,595,756 | A | 1/1997 | Bally et al. | |
| 7,235,391 | B2 | 6/2007 | Wu et al. | |
| 7,264,958 | B1 | 9/2007 | Koehl et al. | |
| 7,288,251 | B2 | 10/2007 | Bedian et al. | |
| 9,364,542 | B2 | 6/2016 | Chang | |
| 2002/0061592 | A1 | 5/2002 | Blanche et al. | |
| 2005/0186225 | A1 * | 8/2005 | Evans .................. | A61K 9/0019 424/233.1 |
| 2010/0297072 | A1 | 11/2010 | DePinho | |
| 2011/0034560 | A1 | 2/2011 | Jacobson et al. | |

FOREIGN PATENT DOCUMENTS

| | | | | |
|---|---|---|---|---|
| CA | 2244213 A1 | 8/1997 | | |
| CN | 101381742 A | 3/2009 | | |
| CN | 1961961 B | 5/2010 | | |
| EP | 170269 A2 | 2/1986 | | |
| JP | 2000504334 A | 4/2000 | | |
| JP | 2002541792 A | 12/2002 | | |
| JP | 2008531700 A | 8/2008 | | |
| JP | 2015526450 A | 9/2015 | | |
| WO | WO-1999018799 A1 | 4/1999 | | |
| WO | WO-200032754 A1 | 6/2000 | | |
| WO | WO-2000061726 A1 | 10/2000 | | |
| WO | WO-0111034 A3 | 6/2001 | | |
| WO | WO-2005040220 A1 | 5/2005 | | |
| WO | WO-2005118825 A2 | 12/2005 | | |
| WO | WO-2006093924 A1 | 9/2006 | | |
| WO | WO-2013026833 A1 | 2/2013 | | |
| WO | WO-2013164754 A2 | 11/2013 | | |
| WO | WO-2014029702 A1 | 2/2014 | | |
| WO | WO-2015040234 A1 | 3/2015 | | |
| WO | WO-2015059303 A1 | 4/2015 | | |
| WO | WO-2015059465 A1 | 4/2015 | | |
| WO | WO-2015153912 A1 | 10/2015 | | |
| WO | WO-2016030489 A3 | 4/2016 | | |
| WO | WO-2016174200 A1 * | 11/2016 | ........... | A61K 35/761 |
| WO | 2017161360 A2 | 9/2017 | | |
| WO | WO-2018075978 A1 | 4/2018 | | |

OTHER PUBLICATIONS

Nema, et al. PDA J Pharm Sci Technol. May-Jun. 2011;65(3):287-332. PMID: 22293237. (Year: 2011).*

Golvanov, et al. J Am Chem Soc. Jul. 28, 2004; 126(29):8933-9. PMID: 15265823. (Year: 2004).*

Kennedy and Parks, "Adenovirus Virion Stability and the Viral Genome: Size Matters," Mol Ther. 2009; 17 (10):1664-1666.

Ma and Lu, "Receptors for human adenoviruses," Journal of Microbes and Infections. 2008;4(4):238-242.

Nicklin et al., "The influence of adenovirus fiber structure and function on vector development for gene therapy," Mol Ther. 2005;12(3):384-93.

Nema S, Brendel RJ. Excipients and their role in approved injectable products: current usage and future directions. Pda J Pharm Sci Technol. May-Jun. 2011;65(3):287-332. doi: 10.5731/pdajpst.2011.00634. PMID: 22293237. (Year: 2011).

Golovanov AP, Hautbergue GM, Wilson SA, Lian LY. A simple method for improving protein solubility and long-term stability. J Am Chem Soc. Jul. 28, 2004;126(29):8933-9. doi: 10.1021/ja049297h. PMID: 15264823. (Year: 2004).

(Continued)

*Primary Examiner* — Benjamin P Blumel
*Assistant Examiner* — Jeffrey Mark Sifford
(74) *Attorney, Agent, or Firm* — COOLEY LLP; Andrew T. Wilkins; David M. Lee

(57) ABSTRACT

The present disclosure relates to formulations suitable for the storage of group B adenoviruses, such as Enadenotucirev (EnAd), processes for making the formulations, and use of the formulations in methods of treatment.

15 Claims, 15 Drawing Sheets

Specification includes a Sequence Listing.

(56) References Cited

OTHER PUBLICATIONS

Chang, C-M, et al., Treatment of hepatocellular carcinoma with adeno-associated virus encoding interleukin-15 superagonist, Hum Gene Ther. May 2010;21(5):611-21.
Cheng, L., et al., Hyper-IL-15 suppresses metastatic and autochthonous liver cancer by promoting tumour-specific CD8+ T cell responses, J Hepatol. Dec. 2014;61(6):1297-303.
Guo, Y., et al, Immunobiology of the IL-15/IL-15Ra complex as an antitumor and antiviral agent, Cytokine Growth Factor Rev. Dec. 2017:38:10-21.
Ni, S., et al., Evaluation of biodistribution and safety of adenovirus vectors containing group B fibers after intravenous injection into baboons, Hum Gene Ther. Jun. 2005:16(6):664-77.
International Search Report of PCT/EP2022/053477, dated Jun. 7, 2022.
Nemunaitis, J., et al., Intravenous infusion of a replication-selective adenovirus (ONYX-015) in cancer patients: safety, feasibility and biological activity, Gene Therapy (2001) 8, 746-759.
Riedmann, Human Vaccines: News, Human Vaccines & Immunotherapeutics (2012), 8(11):1550-1553.
Auerbach et al, Angiogenesis Assays; Problems and Pitfalls, Cancer and Metastasis Reviews (2000), 19:167-172.
Beans, Targeting Metastasis to Halt Cancers Spread, PNAS (Dec. 11, 2018), 115 (50):12539-12543.
Gravanis et al., TPA as a Therapeutic Target in Stroke, Expert Opin Ther Targets (Feb. 2008), 12(2):1-18.
Gura, Systems for Identifying New Drugs Are Often Faulty, Science (Nov. 7, 1997), 278:1041-1042.
Hait, Anticancer Drug Development: the Grand Challenges, Nature Reviews Drug Discovery (Apr. 2010), 9:253-254.
Jain, Barriers to Drug Delivery in Solid Tumors, Scientific American (Jul. 1994), 58-65.
Sporn et al., Chemoprevention of Cancer, Carcinogenesis (2000), 21(3):525-530.
International Search Report and Written Opinion for PCT/EP2019/052398, mailed Jun. 7, 2019.
Nakashima, E., et al., A candidate for cancer gene therapy: MIP-1 alpha gene transfer to an adenocarcinoma cell line-educed tumorigenicity and induced protective immunity in immunocompetent mice, Pharm Res. Dec. 1996; 13 12):1896-901.
Kaufman, H. L, et al., Oncolytic viruses: a new class of immunotherapy drugs, Nat Rev Drug Discov. Sep. 2015; 14 (9):642-62.
Ferrantini, M., et al., Interferon-alpha and cancer: mechanisms of action and new perspectives of clinical use, Biochimie. Jun.-Jul. 2007;89(6-7):884-93.
Plasmids 101: Multicistronic Vectors. Jan. 29, 2015, https://web.archive.org/web/20150129022727/https://blog.addgene.org/plasmids-101-multicistronic-vectors.
Gene Therapy Vaccinia Virus Vectors Explained. Feb. 1, 2015, https://web.archive.org/web/20150201083914/www.genetherapynet.com/viral-vector/vaccinia-viruses.html.
International Search Report and Written Opinion of PCT/EP2020/067668, dated Nov. 5, 2020.
Detergents: Triton X-100, Tween-20, and More, 2020-06-10, Mater Methods 2013;3:163.
Clement, N., et al, Construction and production of oncotropic vectors, derived from MVM(p), that share reduced sequence homology with helper plasmids, Cancer Gene Ther. Sep. 2002;9(9):762-70.
Shashkova, E., et al, Characterization of human adenovirus serotypes 5, 6, 11, and 35 as anticancer agents, Virology Nov. 25, 2009;394(2):311-20.
Ferguson, M., et al, Systemic delivery of oncolytic viruses: hopes and hurdles, Advances in Virology, V 2012, Article ID 805629.
Carlisle, R.C., et al., Human erythrocytes bind and inactivate type 5 adenovirus by presenting Coxsackie virus-adenovirus receptor and complement receptor 1, Blood Feb. 26, 2009;113(9):1909-18.
Chau, L.A, et al., HuM291(Nuvion), a humanized Fc receptor-nonbinding antibody against CD3, anergizes peripheral blood T cells as partial agonist of the T cell receptor, Transplantation Apr. 15, 2001;71(7):941-50.
Diehl, K-H., et al., A Good Practice Guide to the Administration of Substances and Removal of Blood, Including Routes and Volumes, J. Appl. Toxicol. 21, 15-23 (2001).
Hemminki et al., AD3-HTERT-E1A, a Fully Serotype 3 Oncolytic Adenovirus, in Patients With Chemotherapy Refractory Cancer, Molecular Therapy (Aug. 7, 2012),20(9):1810-1830.
Hotte et al., An Optimized Clinincal Regimen for the Oncolyticvirus PV701, Clinical Cancer Research (Feb. 1, 2007), 13(3):977-985.
Nemunaitis et al., Intravenous Infusion of a Replication-Selective Adenovirus (ONYX-015) in Cancer Patients: Safety, Feasibility and Biological Activity, Gene Therapy (2001), 8:746-759.
Small et al., A Phase I Trial of Intravenous CG7870, a Replication-Selective, Protate-Specific Antigen-Targeted Oncolytic Adenovirus, for the Treatment of Hormone-Refractory, Metastatic Prostate Cancer, Molecular Therapy (Jul. 2006), 14(1):107-117.
European Patent Office, Opposition Division, Decision Revocation of the European Patent No. EP 3007711, Feb. 21, 2023, Munich, Germany.
European Patent Office, Opposition Division, Consolidated List of Cited Opposition 7 Documents, European Patent No. EP 3007711, Dec. 1, 2022, Munich, Germany.
Fisicaro et al, Versatile Co-Expression of Graft-Protective Proteins Using 2A-Linked Assettes, Xenotransplantation (2011), 18(2):121-130.

* cited by examiner

Figure 1
A Stored at 2-8°C
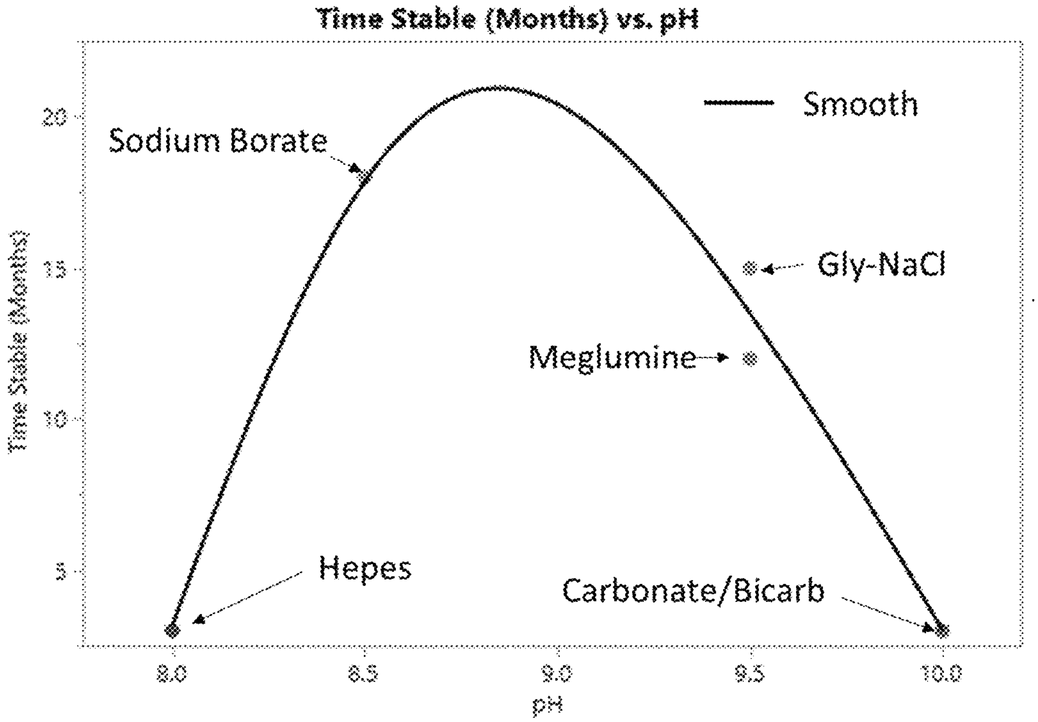
B Accelerated Conditions 25°C
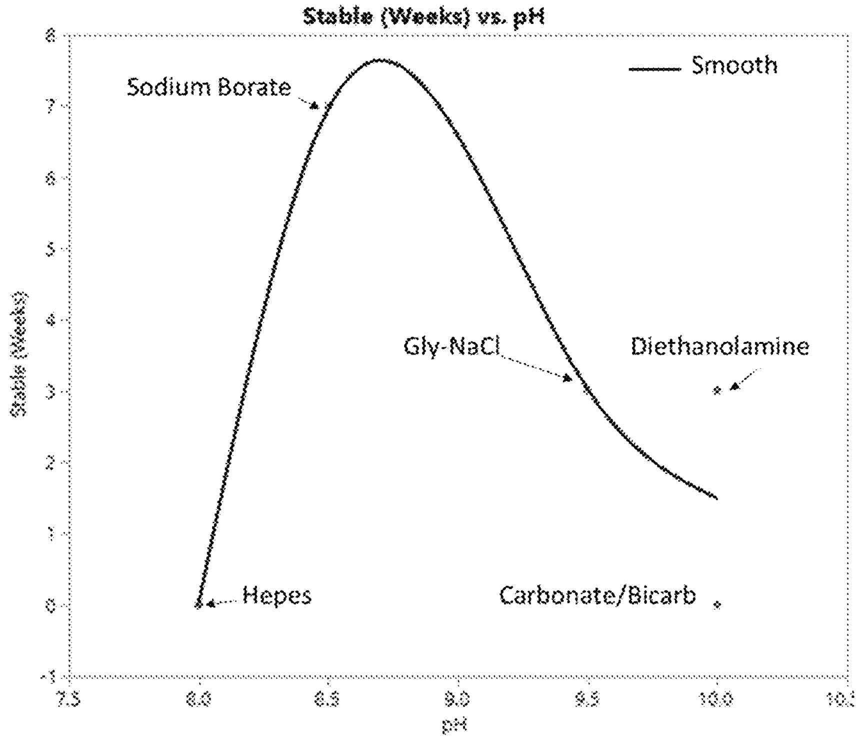

Figure 2 Accelerated Design of Experiments (DOE) Showing 15-20% Glycerol is Beneficial
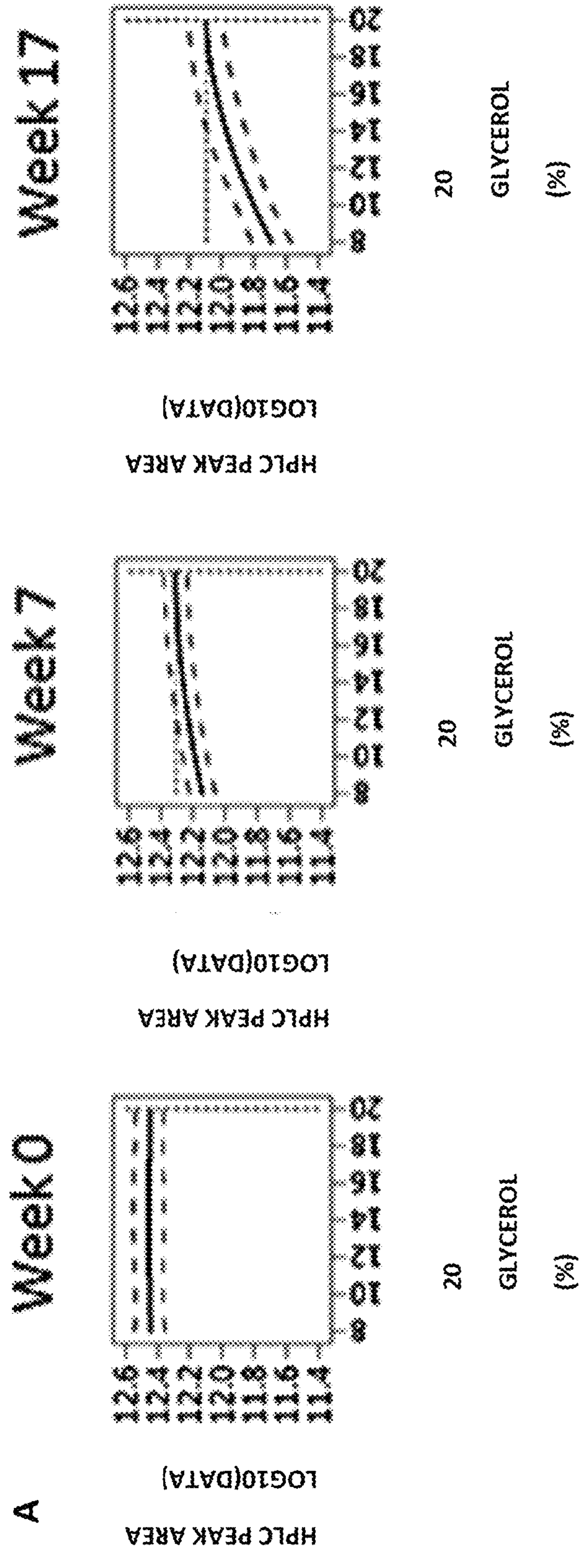

Figure 2 cont.
B 10Mm HEPES, with Glycerol/Accelerated Conditions
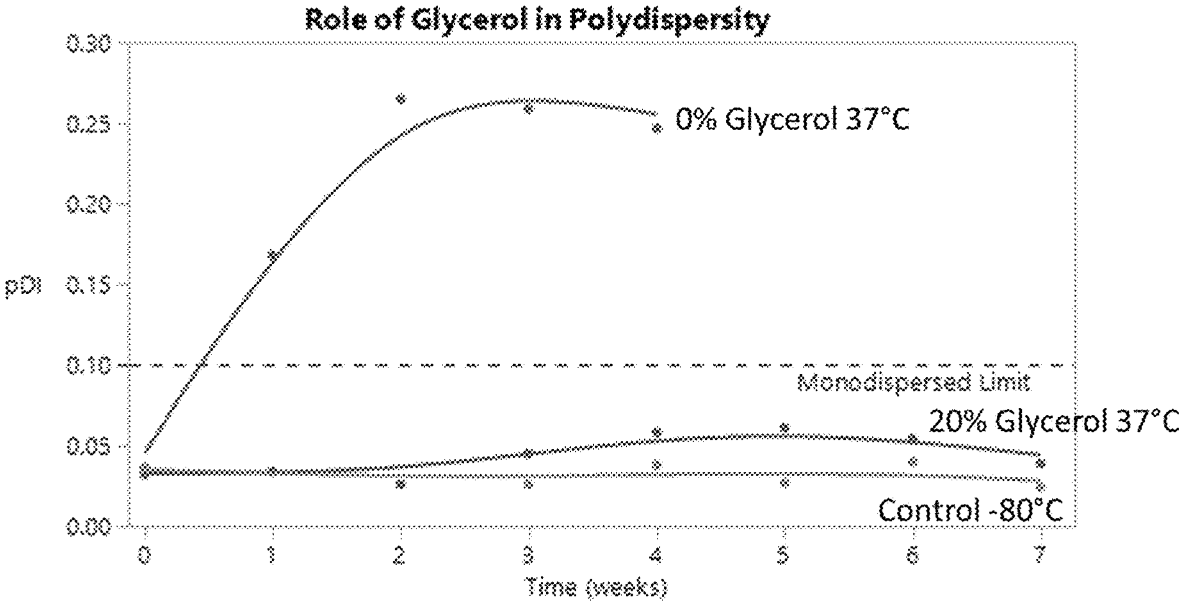
C 10Mm HEPES with Glycerol Stored at 25°C
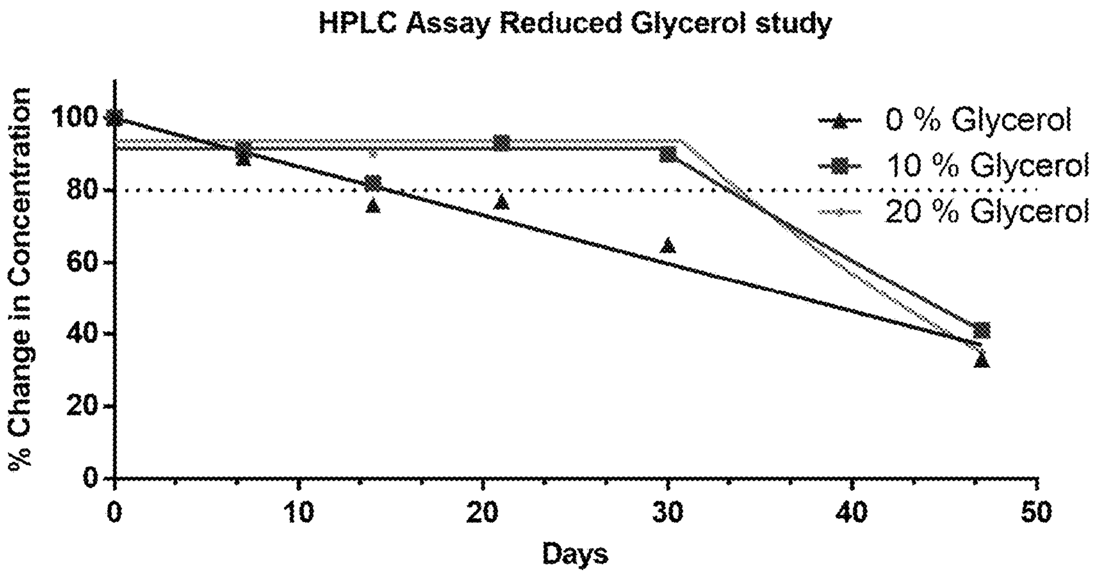

Figure 3
A 20% Glycerol and buffer at pH9 with HEPES control and stored at 4°C (no ethanol)
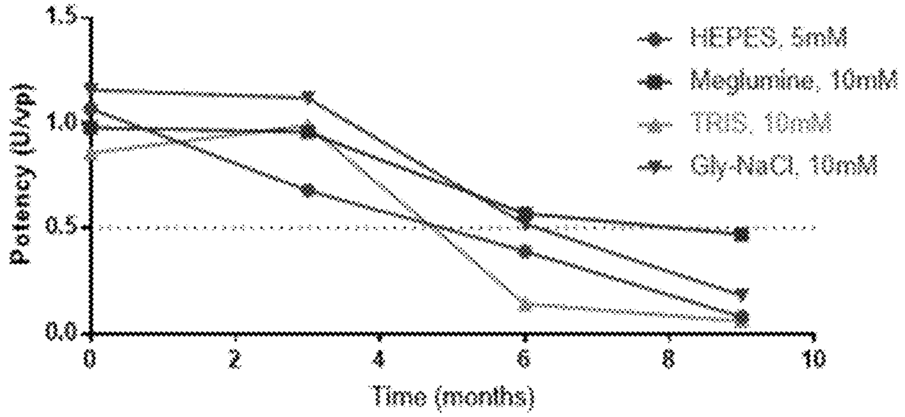
B 20% Glycerol and buffer at pH9 and 4°C (no ethanol)
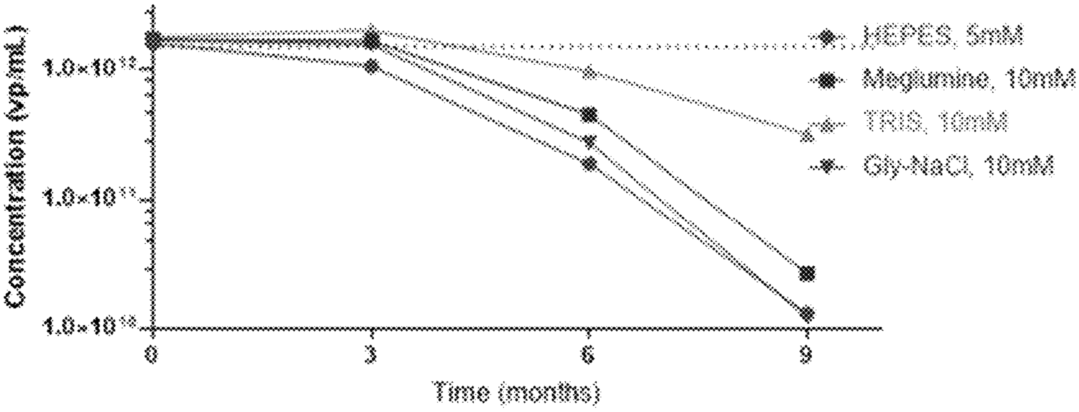
C 20% Glycerol, Meglumine or Gly-NaCl, Ethanol, Methionine, Polysobrate at pH9 and 4°C, HPLC analysis of conc. vp/ml
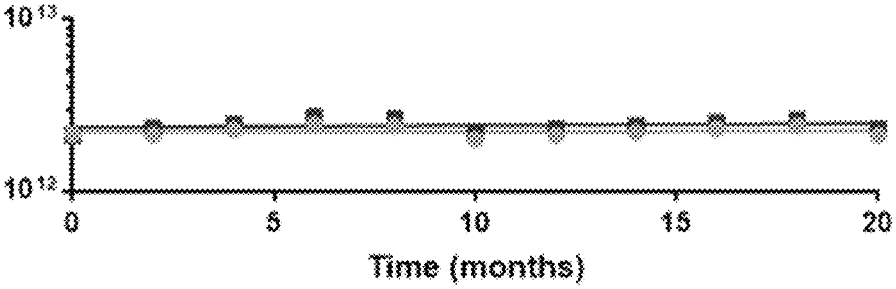

C
5mM HEPES, 17 % Glycerol, 1 % EtOH, 0.15mM Met, pH 8.0
Relative potency (U/vp)
1.5
1.0
0.5
0.0
0
5
10
15
20
25
30
Time (months)
D
5mM HEPES, 17 % Glycerol, 1 % EtOH, 0.15mM Met, 10mM Arg, pH 8.0
Relative potency (U/vp)
1.5
1.0
0.5
0.0
0
5
10
15
20
25
30
Time (months)

Concentration (Buffering agent, 20% glycerol, 1.4%EtOH, 15mM Arg, 0.25mM Met, 0.15% PS 80, 25°C)

- Gly-NaCl, pH 9
- TRIS, pH 8
- TRIS, pH 8.8
- Meglumine, pH 8
- Meglumine, pH 8.5
- Meglumine, pH 9
- HEPES, pH 8

Time (weeks)

Concentration (vp/mL)

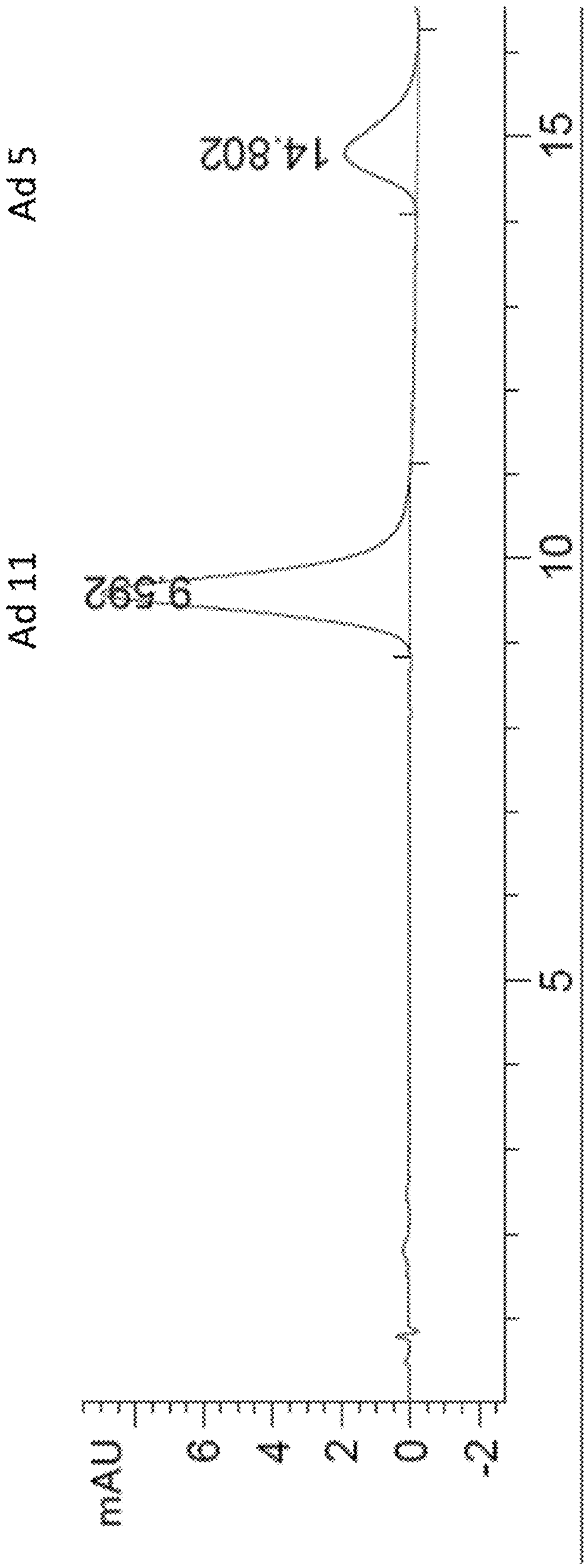
Figure 7 Analytical Separation of Adenovirus 5 (Ad 5) and Adenovirus 11 (Ad 11) by Anion Exchange Chromatography Oncolytic Relative Potency Analysis (Buffering agent, 20% glycerol, 1.4% ethanol, 15 mM arginine, 0.25 mM methionine) 4°C storage Ratio of Total:Infectious Viral Particles Analysis (Buffering agent, 20% glycerol, 1.4% ethanol, 15 mM arginine, 0.25 mM methionine), 4°C storage

Figure 8C Oncolytic Relative Potency Analysis (Buffering Agent, 20% glycerol, 1.4% ethanol, 15 mM arginine, 0.25 mM methionine)
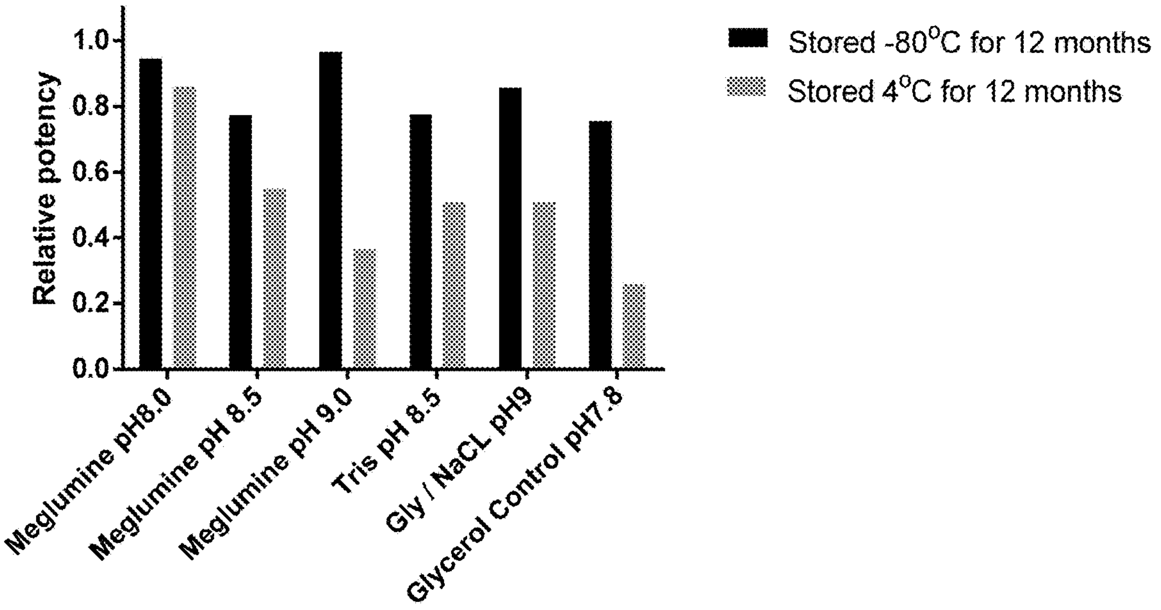
Figure 8D Virus Concentration by AEX-HPLC Analysis (Buffering Agent, 20% glycerol, 1.4% ethanol, 15 mM arginine, 0.25 mM methionine)
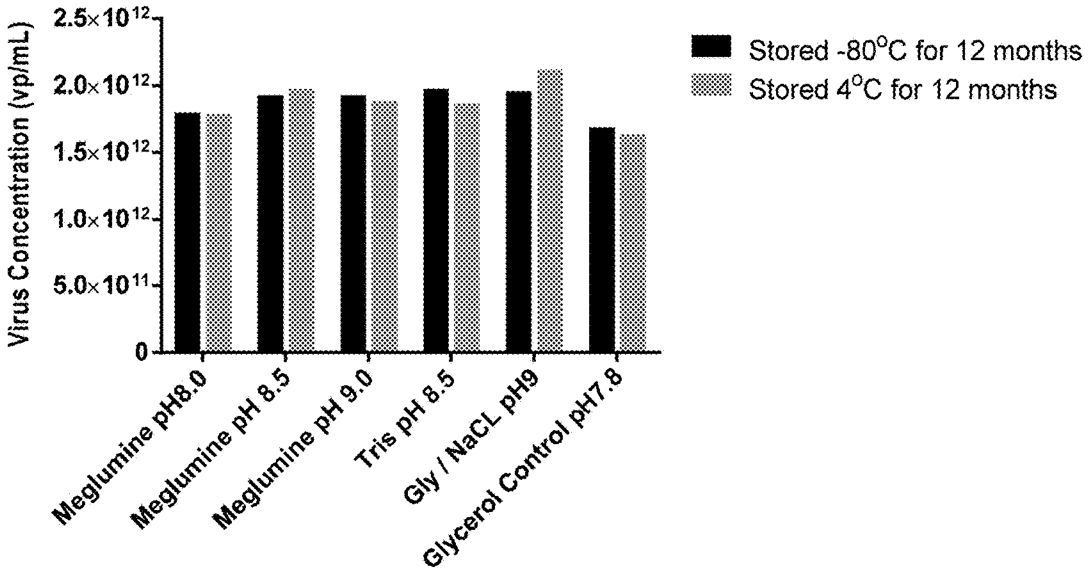

Ratio of total virus: infectious virus particles (Buffering Agent, 20% glycerol, 1.4% ethanol, 15 mM arginine, 0.25 mM methionine)

GROUP B ADENOVIRUS-CONTAINING FORMULATION

CROSS-REFERENCE TO RELATED APPLICATIONS

The present application is a continuation application of U.S. patent application Ser. No. 16/965,549, filed Jul. 28, 2020, which is a 35 U.S.C. § 371 national phase application from International Application No. PCT/EP2019/052398, filed Jan. 31, 2019, and published under PCT Article 21(2) in English, which designated the U.S., and claims the benefit of priority from United Kingdom Patent Application No. GB1801614.7 filed on Jan. 31, 2018, each of which prior applications are incorporated by reference herein into this application in their entirety including all tables, figures and claims.

SEQUENCE LISTING

The instant application contains a Sequence Listing which has been submitted in XML format via Patent Center and is hereby incorporated by reference in its entirety. Said XML copy, created on Apr. 18, 2024, is named 249USC1_seqlist.xml and is 1,893,608 bytes in size.

The present disclosure relates to a formulation of a group B adenovirus, such as enadenotucirev (EnAd), a process of making the formulation and use the formulation in treatment, in particular treatment of cancer.

BACKGROUND

At the present time the pharmaceutical field is on the edge of realising the potential of viruses as therapeutics for human use. To date a virus derived from dl1520, also referred to as ONYX-015 or CI-1042 and developed by ONYX Pharmaceuticals™ and acquired by Shanghai Sunway Biotech, is approved for use in head and neck cancer in a limited number of countries and Imlygic® (Talimogene laherparepvec) has been approved for the treatment of melanoma. However, there are a number of viruses currently in the clinic, which should hopefully result in some of these being registered for use in humans.

A number of virus therapies are based on adenoviruses, such as Group B adenoviruses, for example EnAd. EnAd (previously known as ColoAd1) is a chimeric oncolytic adenovirus (WO2005/118825) currently in clinical trials for the treatment of epithelial cancer. These adenoviral based therapeutic agents need to be manufactured in quantities suitable for supporting both the clinical trials and demand after registration and under conditions that adhere to good manufacturing practice (GMP).

Adenoviral formulations for long term storage are known in the art, see for example U.S. Pat. Nos. 7,888,096 and 7,351,415. Such formulations have been used to suspend Group C adenoviruses such as Ad5, in particular replication deficient Ad5 viruses engineered to express human p53.

Group B adenoviruses have different properties to group C adenoviruses, for example the group B viruses infect cells via CD46, whereas group C viruses infect cell via the CAR receptor (coxsackievirus and adenovirus receptor). The group B viruses have a different retention time to group C viruses when analysed by high performance liquid chromatography. See for example FIG. 7, which shows the relative retention times of Ad5 and Ad11 type viruses (such as EnAd).

The present inventors have found that when prior art formulations are used to suspend Group B adenoviruses, such as EnAd, the adenoviruses can only be kept at 4° C. for very short periods of time before significant degradation in both virus concentration and potency occurs. This type of degradation is referred to as chemical degradation because it stems from chemical processes that occur in the formulation.

Physical stability is also very important, for example physical instability may manifest itself by aggregation, which may result in increased immunogenicity.

Accordingly, there is a need for an improved formulation specifically tailored for longer term storage of Group B adenoviruses, for example formulations suitable for storage at 4° C. This allows the formulations to be kept for longer periods at 4° C., with minimal detrimental effects on the potency and viability of the adenoviruses. This in turn makes the formulations considerably easier and cheaper to store and to transport, for example from a manufacturing facility to the clinic.

Surprisingly the present inventors have established that whilst a number of ingredients are important to the stabilisation of the group B virus formulation a small amount of ethanol seems to be essential to minimising degradation and maintaining infectivity.

The present disclosure provides a combination of ingredients, which together act to stabilise group B viruses, such as EnAd, in particular at 4° C.

SUMMARY OF THE INVENTION

The present disclosure provides formulations suitable for the storage of group B adenoviruses, for example a group B virus encoding at least one transgene, and is summarised in the following paragraphs:

1. A liquid formulation suitable for a group B adenovirus, comprising:
   a) a group B adenovirus, such as replication competent group B adenovirus,
   b) 15 to 25% v/v glycerol, (for example 17 to 20% v/v), such as 16, 17, 18, 19, 20, 21% v/v glycerol; and
   c) 0.1 to 1.6% v/v ethanol, for example 0.1-1.5%, such as 1% v/v ethanol or alternatively 1.4% or 1.5% v/v;
   d) a buffer,
   wherein the pH of the formulation is in the range 8.0 to 9.6, for example 8.0, 8.1, 8.2, 8.3, 8.4, 8.5, 8.6, 8.7, 8.8, 8.9, 9.0, 9.1, 9.2, 9.3, 9.4 or 9.5, such as 8.5 to 9.5, in particular 8.5 to 9.0, more specifically pH8.5, 8.6, 8.7, 8.8 or 8.9.
2. The formulation according to paragraph 1, wherein the pH is 8.0.
3. The formulation according to paragraph 1, wherein the pH is 8.1.
4. The formulation according to paragraph 1, wherein the pH is 8.2.
5. The formulation according to paragraph 1, wherein the pH is 8.3.
6. The formulation according to paragraph 1, wherein the pH is 8.4.
7. The formulation according to paragraph 1, wherein the pH is 8.5.
8. The formulation according to paragraph 1, wherein the pH is 8.6.
9. The formulation according to paragraph 1, wherein the pH is 8.7.
10. The formulation according to paragraph 1, wherein the pH is 8.8.

11. The formulation according to paragraph 1, wherein the pH is 8.9.
12. The formulation according to paragraph 1, wherein the pH is 9.
13. The formulation according to any one of paragraphs 1 to 12, wherein the formulation is for administration by intravenous administration, for example after dilution with a liquid for injection, such an isotonic solution or water for injection.
14. The formulation according to paragraph 13, wherein the formulation is for administration by slow injection.
15. The formulation according to paragraph 13, wherein the formulation is for administration by infusion.
16. The formulation according to any one of paragraphs 1 to 15 further comprising a surfactant, for example a nonionic surfactant.
17. The formulation according to paragraph 16, further comprising polysorbate, for example polysorbate 20, 40, 60, or 80, such as 0.05-0.15% v/v polysorbate 20, 40, 60, or 80.
18. The formulation according to paragraph 17, wherein the formulation comprises polysorbate 80, for example 0.05-0.15% v/v polysorbate 80, such as 0.115% v/v polysorbate 80.
19. The formulation according to any one of paragraphs 1 to 18, further comprising methionine, for example 0.01-0.3 mM, such as 0.01 to 0.25, in particular 0.25 mM methionine.
20. The formulation according to any one of paragraph 1 to 18, further comprising methionine, for example 0.01-0.3 mM, for example 0.01 to 0.2, such as 0.15 mM methionine.
21. The formulation according to any one of paragraphs 1 to 20, further comprising 5 to 20 mM, such as 15 mM arginine.
22. The formulation according to any one of paragraphs 1 to 20, further comprising arginine, for example 5 to 15 mM, such as 10 mM arginine.
23. The formulation according to any one of paragraphs 1 to 20, wherein the buffer is selected from meglumine, Gly-NaCl, and TRIS.
24. The formulation according to paragraph 23, wherein the formulation comprises meglumine buffer.
25. The formulation according to any one of paragraphs 1 to 24, wherein the formulation does not comprise HEPES buffer.
26. The formulation according to any one of paragraphs 1 to 15, wherein the formulation comprises:
    a) 15-20% v/v glycerol;
    b) 1-1.5% v/v ethanol;
    c) 0.2-0.3 mM methionine;
    d) 10-20 mM arginine; and
    e) a buffer, such as meglumine; and
    f) optionally 0.1-0.2% v/v polysorbate 80;
    wherein the pH of the formulation is at a pH in the range 8.0 to 9.5, for example 8.0 to 9.0, such as pH 8.0, 8.1, 8.2, 8.3, 8.4, 8.5, 8.6, 8.7, 8.8, 8.9 or 9.0, in particular 8.0
27. The formulation according to paragraph 26, wherein the formulation comprises
    a) 20% v/v glycerol;
    b) 1.4-1.5% v/v ethanol;
    c) 0.25 mM methionine;
    d) 15 mM arginine; and
    e) a buffer, such as meglumine;
    wherein the pH of the formulation is at a pH in the range 8.0 to 9.5, for example 8.0 to 9.0, such as pH 8.0, 8.1, 8.2, 8.3, 8.4, 8.5, 8.6, 8.7, 8.8, 8.9 or 9.0, in particular 8.0
28. The formulation according to any one of paragraphs 1 to 15, wherein the formulation comprises:
    a) 20% v/v glycerol;
    b) 1% v/v ethanol;
    c) 0.115% v/v polysorbate 80;
    d) 0.15 mM methionine;
    e) 10 mM arginine; and
    f) a buffer, such as meglumine;
    wherein the pH of the formulation is at a pH in the range 8.0 to 9.5, for example 8.5 to 9.5, such as pH 8.0, 8.1, 8.2, 8.3, 8.4, 8.5, 8.6, 8.7, 8.8, 8.9 or 9.0, in particular 9.0.
29. The formulation according to any one of the preceding paragraphs, wherein the group B adenovirus comprises a sequence of formula (I):

$$5'ITR-B_1-B_A-B_2-B_X-B_B-B_Y-B_3-3'ITR$$

wherein:
    $B_1$ is bond or comprises: E1A, E1B or E1A-E1B;
    $B_A$ comprises -E2B-L1-L2-L3-E2A-L4;
    $B_2$ is a bond or comprises: E3;
    $B_X$ is a bond or a DNA sequence comprising: a restriction site, one or more transgenes or both;
    $B_B$ comprises L5;
    $B_Y$ is a bond or a DNA sequence comprising: a restriction site, one or more transgenes or both;
    $B_3$ is a bond or comprises: E4;
    wherein at least one of $B_X$ or $B_Y$ is not a bond.
30. The formulation according to paragraph 29, wherein $B_X$ comprises a transgene or transgene cassette.
31. The formulation according to paragraphs 29 or 30, wherein $B_Y$ comprises a transgene or transgene cassette.
32. The formulation according to paragraph 29, wherein $B_Y$ comprises a transgene or transgene cassette and $B_X$ is a bond.
33. The formulation according to any one of paragraphs 29 to 32, wherein the one or more transgenes or transgene cassette is under the control of an endogenous or exogenous promoter, such as an endogenous promotor.
34. The formulation according to paragraph 33, wherein the transgene cassette is under the control of an endogenous promoter selected from the group consisting of E4 and major late promoter, in particular the major late promoter.
35. The formulation according to any one of paragraphs 29 to 34, wherein the transgene cassette further comprises a regulatory element independently selected from:
    a) a splice acceptor sequence (for example a short splice acceptor sequence CAGG, SEQ ID NO: 1 or SEQ ID NO: 2),
    b) an internal ribosome entry sequence or a high self-cleavage efficiency 2A peptide,
    c) a Kozak sequence, and
    d) combinations thereof.
36. The formulation according to paragraph 35, wherein the transgene cassette comprises a Kozak sequence is at the start of the protein coding sequence.
37. The formulation according to any one of paragraphs 29 to 36, wherein the transgene cassette encodes a high self-cleavage efficiency 2A peptide, for example a P2A peptide, E2A peptide, F2A peptide and T2A peptide.

38. The formulation according to paragraph 37, wherein the transgene cassette encodes multiple high self-cleavage efficiency 2A peptides, such as 2, 3 or 4 peptides.

39. The formulation according to paragraph 38, wherein self-cleavage peptides are encoded by non-identical DNA sequences.

40. The formulation according to any one of paragraphs 29 to 39, wherein the transgene cassette further comprises a polyadenylation sequence.

41. The formulation according to any one of paragraphs 29 to 40, wherein the transgene cassette further comprises a sequence encoding a leader sequence.

42. The formulation according to any one of paragraphs 29 to 41, wherein the transgene cassette further comprises a restriction site at the 3'end of the DNA sequence and/or at the 5'end of the DNA sequence.

43. The formulation according to any of paragraphs 29 to 42, wherein at least one transgene cassette encodes monocistronic mRNA.

44. The formulation according to any one of paragraphs 29 to 43, wherein at least one transgene cassette encodes a polycistronic mRNA.

45. The formulation according to any one of paragraphs 29 to 44, wherein the transgene encodes an RNAi sequence, a polypeptide (such as protein or peptide).

46. The formulation according to paragraph 45, wherein the polypeptide is an antibody or binding fragment thereof.

47. The formulation according to paragraph 46, wherein the antibody or binding fragment thereof is specific to OX40, OX40 ligand, CD27, CD28, CD30, CD40, CD40 ligand, CD70, CD137, GITR, 4-1BB, ICOS, ICOS ligand, CTLA-4, PD-1, PD-L1, PD-L2, VISTA, B7-H3, B7-H4, HVEM, ILT-2, ILT-3, ILT-4, TIM-3, LAG-3, BTLA, LIGHT, CD160, CTLA-4, PD-1, PD-L1, PD-L2, for example CD40 and CD40 ligand.

48. The formulation according to any one of paragraphs 45 to 47, wherein the encoded polypeptide is a cytokine independently selected from the group comprising IL-1α, IL-1β, IL-6, IL-9, IL-12, IL-13, IL-17, IL-18, IL-22, IL-23, IL-24, IL-25, IL-26, IL-27, IL-33, IL-35, IL-2, IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF, for example IL-12, IL-18, IL-22, IL-7, IL-15, IL-21, IFNγ, TNFα, TGFβ and lymphotoxin α (LTA).

49. The formulation according to any one of paragraphs 24 to 44, wherein the encoded polypeptide is a independently selected from the group comprising IL-8, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and CRTH2, for example CCL5, CXCL9, CXCL12, CCL2, CCL19, CCL21, CXCR2, CCR2, CCR4 and CXCR4 or a receptor thereof (such as a chemokine selected from IL-8, CCL5, CCL17, CCL20, CCL22, CXCL9, CXCL10, CXCL11, CXCL13, CXCL12, CCL2, CCL19, CCL21 or a receptor thereof, more specifically CCL5, CXCL9, CXCL12, CCL2, CCL19, CCL21 or a receptor thereof).

50. The formulation according to any one of paragraphs 29 to 49, wherein the encoded polypeptide is a reporter gene, for example sodium iodide symporter, intracellular metalloproteins, HSV1-tk, GFPs, luciferase or estrogen receptor, for example sodium iodide symporter.

51. The formulation according to the paragraph 50, wherein the reporter gene is fluorescent protein.

52. The formulation according to any one of paragraphs 1 to 51, wherein the E4orf4 region of the adenovirus is non-functional, for example fully deleted, partially deleted or truncated.

53. The formulation according to any one of paragraphs 1 to 48, wherein the E2B region of the adenovirus is chimeric, for example wherein the E2B region comprises a nucleic acid sequence derived from a first adenoviral serotype and a nucleic acid sequence derived from a second distinct adenoviral serotype; wherein said first and second serotypes are each selected from the adenoviral subgroups B, C, D, E, or F.

54. The formulation according to any one of paragraphs 1 to 53, wherein the adenovirus is chimeric EnAd.

55. The formulation according to any one of paragraphs 1 to 54, wherein the adenovirus is Ad11.

56. The formulation according to any one of paragraphs 1 to 55, wherein the group B adenovirus is replication competent.

57. The formulation according to any one of paragraphs 1 to 56, wherein the virus is shown in SEQ ID NO: 14 or a derivative thereof, for example without a His-tag.

58. The formulation according to any one of paragraphs 1 to 57, wherein the virus is shown in SEQ ID NO: 15 or a derivative thereof, for example with or without a His-tag.

59. The formulation according to any one of paragraphs 1 to 58, wherein the virus is shown in SEQ ID NO: 16 or a derivative thereof, for example with or without a His-tag.

60. The formulation according to any one of paragraphs 1 to 59, wherein the virus is shown in SEQ ID NO: 17 or a derivative thereof, for example with or without a His-tag.

61. The formulation according to any one of paragraphs 1 to 60, wherein the virus is shown in SEQ ID NO: 18 or a derivative thereof, for example with or without a His-tag.

62. The formulation according to any one of paragraphs 1 to 61, wherein the virus is shown in SEQ ID NO: 19 or a derivative thereof, for example with or without a His-tag.

63. The formulation according to any one of paragraphs 1 to 62, wherein the virus is shown in SEQ ID NO: 20 or a derivative thereof, for example with or without a His-tag.

64. The formulation according to any one of paragraphs 1 to 63, wherein the virus is shown in SEQ ID NO: 21 or a derivative thereof, for example with or without a His-tag.

65. The formulation according to any one of paragraphs 1 to 64, wherein the virus is shown in SEQ ID NO: 22 or a derivative thereof, for example with or without a His-tag.

66. The formulation according to any one of paragraphs 1 to 65, wherein the virus is shown in SEQ ID NO: 23 or a derivative thereof, for example with or without a His-tag.

67. The formulation according to any one of paragraphs 1 to 66, wherein the virus is shown in SEQ ID NO: 24 or a derivative thereof, for example with or without a His-tag.
68. The formulation according to any one of paragraphs 1 to 67, wherein the virus is shown in SEQ ID NO: 25 or a derivative thereof, for example with or without a His-tag.
69. The formulation according to any one of paragraphs 1 to 68, wherein the virus is shown in SEQ ID NO: 26 or a derivative thereof, for example with or without a His-tag.
70. The formulation according to any one of paragraphs 1 to 69, wherein the virus is shown in SEQ ID NO: 27 or a derivative thereof, for example with or without a His-tag.
71. The formulation according to any one of paragraphs 1 to 70, wherein the virus is shown in SEQ ID NO: 28 or a derivative thereof, for example with or without a His-tag.
72. The formulation according to any one of paragraphs 1 to 71, wherein the virus is shown in SEQ ID NO: 29 or a derivative thereof, for example with or without a His-tag.
73. The formulation according to any one of paragraphs 1 to 72, wherein the virus is shown in SEQ ID NO: 30 or a derivative thereof, for example with or without a His-tag.
74. The formulation according to any one of paragraphs 1 to 73, wherein the virus is shown in SEQ ID NO: 31 or a derivative thereof, for example with or without a His-tag.
75. The formulation according to any one of paragraphs 1 to 74, wherein the virus is shown in SEQ ID NO: 32 or a derivative thereof, for example with or without a His-tag.
76. The formulation according to any one of paragraphs 1 to 75, wherein the virus is shown in SEQ ID NO: 33 or a derivative thereof, for example with or without a His-tag.
77. The formulation according to any one of paragraphs 1 to 76, wherein the virus is shown in SEQ ID NO: 34 or a derivative thereof, for example with or without a His-tag.
78. The formulation according to any one of paragraphs 1 to 77, wherein the virus is shown in SEQ ID NO: 35 or a derivative thereof, for example with or without a His-tag.
79. The formulation according to any one of paragraphs 1 to 78, wherein the virus is shown in SEQ ID NO: 36 or a derivative thereof, for example with or without a His-tag.
80. The formulation according to any one of paragraphs 1 to 79, wherein the virus is shown in SEQ ID NO: 37 or a derivative thereof, for example with or without a His-tag.
81. The formulation according to any one of paragraphs 1 to 80, wherein the virus is shown in SEQ ID NO: 38 or a derivative thereof, for example with or without a His-tag.
82. The formulation according to any one of paragraphs 1 to 81, wherein the virus is shown in SEQ ID NO: 39 or a derivative thereof, for example with or without a His-tag.
83. The formulation according to any one of paragraphs 1 to 82, wherein the virus is shown in SEQ ID NO: 40 or a derivative thereof, for example with or without a His-tag.
84. The formulation according to any one of paragraphs 1 to 83, wherein the virus is shown in SEQ ID NO: 41 or a derivative thereof, for example with or without a His-tag.
85. The formulation according to any one of paragraphs 1 to 84, wherein the virus is shown in SEQ ID NO: 42 or a derivative thereof, for example with or without a His-tag.
86. The formulation according to any one of paragraphs 1 to 85, wherein the virus is shown in SEQ ID NO: 43 or a derivative thereof, for example with or without a His-tag.
87. The formulation according to any one of paragraphs 1 to 86, wherein the virus is shown in SEQ ID NO: 44 or a derivative thereof, for example with or without a His-tag.
88. The formulation according to any one of paragraphs 1 to 87, wherein the virus is shown in SEQ ID NO: 45 or a derivative thereof, for example with or without a His-tag.
89. The formulation according to any one of paragraphs 1 to 88, wherein the virus is shown in SEQ ID NO: 46 or a derivative thereof, for example with or without a His-tag.
90. The formulation according to any one of paragraphs 1 to 89, wherein the virus is shown in SEQ ID NO: 47 or a derivative thereof, for example with or without a His-tag.
91. The formulation according to any one of paragraphs 1 to 86, wherein the virus is shown in SEQ ID NO: 48 or a derivative thereof, for example with or without a His-tag.
92. The formulation according to any one of paragraphs 1 to 91, wherein the virus is shown in SEQ ID NO: 49 or a derivative thereof, for example with or without a His-tag.
93. The formulation according to any one of paragraphs 1 to 92, wherein the virus is shown in SEQ ID NO: 50 or a derivative thereof, for example with or without a His-tag.
94. The formulation according to any one of paragraphs 1 to 93, wherein the virus is shown in SEQ ID NO: 51 or a derivative thereof, for example with or without a His-tag.
95. The formulation according to any one of paragraphs 1 to 94, wherein the virus is shown in SEQ ID NO: 52 or a derivative thereof, for example with or without a His-tag.
96. The formulation according to any one of paragraphs 1 to 95, wherein the virus is shown in SEQ ID NO: 53 or a derivative thereof, for example with or without a His-tag.
97. The formulation according to any one of paragraphs 1 to 96, wherein the virus is shown in SEQ ID NO: 54 or a derivative thereof, for example with or without a His-tag.
98. The formulation according to any one of paragraphs 1 to 97, wherein the virus is shown in SEQ ID NO: 55 or a derivative thereof, for example with or without a His-tag.

99. The formulation according to any one of paragraphs 1 to 98, wherein the virus is shown in SEQ ID NO: 56 or a derivative thereof, for example with or without a His-tag.
100. The formulation according to any one of paragraphs 1 to 99, wherein the virus is shown in SEQ ID NO: 57 or a derivative thereof, for example with or without a His-tag.
101. The formulation according to any one of paragraphs 1 to 100, wherein the virus is shown in SEQ ID NO: 58 or a derivative thereof, for example with or without a His-tag.
102. The formulation according to any one of paragraphs 1 to 101, wherein the virus is shown in SEQ ID NO: 59 or a derivative thereof, for example with or without a His-tag.
103. The formulation according to any one of paragraphs 1 to 102, wherein the virus is shown in SEQ ID NO: 60 or a derivative thereof, for example with or without a His-tag.
104. The formulation according to any one of paragraphs 1 to 103, wherein the virus is shown in SEQ ID NO: 61 or a derivative thereof, for example with or without a His-tag.
105. The formulation according to any one of paragraphs 1 to 104, wherein the virus is shown in SEQ ID NO: 62 or a derivative thereof, for example with or without a His-tag.
106. The formulation according to any one of paragraphs 1 to 105, wherein the virus is shown in SEQ ID NO: 63 or a derivative thereof, for example with or without a His-tag.
107. The formulation according to any one of paragraphs 1 to 106, wherein the virus is shown in SEQ ID NO: 64 or a derivative thereof, for example without a His-tag.
108. The formulation according to any one of paragraphs 1 to 107, wherein the virus is shown in SEQ ID NO: 65 or a derivative thereof, for example with or without a His-tag.
109. The formulation according to any one of paragraphs 1 to 108, for use in treatment.
110. The formulation according to paragraph 109, for use in the treatment of cancer, for example colorectal cancer, hepatoma, prostate cancer, pancreatic cancer, breast cancer, ovarian cancer, thyroid cancer, renal cancer, bladder cancer, head and neck cancer or lung cancer.
111. The formulation according to paragraph 109 or 110, for intravenous administration, for example after dilution with a liquid for injection.
112. The formulation according to paragraph 109 or 110, for intratumoral injection.
113. Use of a formulation according to any one of paragraphs 1 to 107 in the manufacture of a medicament for the treatment of cancer, for example colorectal cancer, hepatoma, prostate cancer, pancreatic cancer, breast cancer, ovarian cancer, thyroid cancer, renal cancer, bladder cancer, head and neck cancer or lung cancer.
114. A method of treatment, comprising administering a formulation according to any one of paragraphs 1 to 108 to a patient in need thereof.
115. The method of treatment according to paragraph 114, wherein the patient to be treated has cancer, for example colorectal cancer, hepatoma, prostate cancer, pancreatic cancer, breast cancer, ovarian cancer, thyroid cancer, renal cancer, bladder cancer, head and neck cancer or lung cancer.
116. The method of paragraph 114 or 115, where the formulation is administered by intravenous or intratumoral injection.

Advantageously, the present inventors have established that the formulation as described herein allow group B adenoviruses, such as EnAd, to be successfully stored, for example at 4° C., for long periods of time such as 6 months or more, for example 1 year, 1.5 years and 2 years (in particular 18 to 24 months, such as 18, 19, 20, 21, 22, 23 or 24 months), without significant degradation or reduction in potency. Aggregation may also be minimised in the formulations of the present disclosure. Formulations of the disclosure may also be stable at temperatures such as 25° C. for moderate periods of time.

Long term storage of the virus may, for example be at temperatures such as −60° C. or lower, more specifically in the range −60 to −80° C., in particular −60, −61, −62, −63, −64, −65, −66, −67, −68, −69, −70, −71, −72, −73, −74, −75, −76, −77, −78, −79 and −80.

In one embodiment the formulations of the present disclosure have a pH of 8.5 to 9.5 (such as pH of 8.5, 8.6, 8.7, 8.8, 8.9, 9.0, 9.1, 9.2, 9.3, 9.4 or 9.5) which is significantly higher than physiological pH, i.e. pH 7.4.

In one embodiment, the formulation has a pH of 9.0. Surprisingly, the present inventors have discovered that the high pH has a significant effect on the stability of the group B adenoviruses (such as EnAd) in the formulation.

The concentration of glycerol is also important to the stability of the group B adenoviruses (such as EnAd).

According to the EU Medicines Agency, whilst ethanol is employed in oral and topical pharmaceutical formulations of small chemical entities and homeopathic remedies, there are certain safety concerns around the use of ethanol. Ethanol is a central nervous system depressant. Mild to moderate intoxication in adults can include euphoria, ataxia, sedation, aggressive behaviour, nausea and vomiting. At higher doses it can cause respiratory depression or failure, and cardiotoxicities, such as atrial tachycardia, atrial fibrillation, arrhythmias, AV block, hypotension, congestive heart failure and severe myocardial depression. In children ethanol intoxication can result in hypoglycaemia, hypothermia and comma. Other toxicities after acute exposure include seizures, hypotonia, hyporeflexia, gastrointestinal bleeding, acute hepatitis, acute pancreatitis, rhabdomyolysis, hypokalemia, and lactic acidosis.

Ethanol metabolism varies between individuals and with age, for example some individuals are deficient in the enzyme alcohol dehydrogenase, which reduces their ability to metabolise alcohol. In formulations for intravenous administration the ethanol goes straight into the blood stream, which maximises any toxic effects. In addition, the volumes administered can be large so 500 ml to 1 L of formulation containing 10% of ethanol is 50 to 100 ml of ethanol.

Thus, whilst the ethanol seems to be an important to the stabilising of group B adenovirus formulations it is important that the toxicity of the ethanol is the formulation be minimised. Surprisingly very small amounts of ethanol, for example less than 1.5%, such as less than 1% are sufficient to provide the stabilisation. In one embodiment not more than 1.5% of ethanol is employed, for example not more than 1% is employed. This is beneficial because it minimises the toxicity of the ethanol whilst providing stabilising effects. In addition, it renders the formulations suitable for use in most patient populations.

In one embodiment the formulation of the present disclosure comprises a non-ionic surfactant, for example selected from the group comprising Cetomacrogol™_1000 (also known as Brij® 52, 56 or 58), cetostearyl alcohol, palmitic acid, glycerol monolaurate, oleyl alcohol, poloxamers, Pluronic™_F127 (poloxamer 407), polysorbates (for example polysorbate 20, 40, 60, 80 or 85), stearic acid, sorbitan tristearate. In one embodiment a nonionic surfactant with a hydrophile-lipophile balance in the range 14.5 to 17 is employed.

In one embodiment, the formulation further comprising polysorbate, for example polysorbate 20, 40, 60, or 80, such as 0.05-0.15% polysorbate 20, 40, 60, 80 or a combination of two or more of the same. In one embodiment, the formulation comprises 0.05%, 0.06%, 0.07%, 0.08%, 0.09%, 0.10%, 0.11%, 0.12%, 0.13%, 0.14%, or 0.15% polysorbate 20, 40, 60 80, or a combination of two or more of the same. The advantage of adding polysorbate to the formulation is that polysorbate helps to preserve group B adenovirus potency during long term storage and may minimise aggregation.

In one embodiment, the formulation comprises polysorbate 80, for example 0.05-0.15% polysorbate 80, such as 0.09 to 0.11% polysorbate 80, such as 0.1% or 0.115% polysorbate. In one embodiment, the formulation comprises 0.115% polysorbate.

Advantageously, the non-ionic surfactant, in particular polysorbate (such as polysorbate 80) reduces or inhibits interfacial stress within the formulation, for example reduces surface stress on the virus, which in turn can cause disruption of the virus.

Whilst not wishing to be bound by theory it is thought that the addition of certain amino acids, for example methionine, arginine and combinations thereof to the formulation may reduce virus/virus interaction and thereby contribute to stabilising the distribution of group B adenovirus in the formulation, for example by providing steric protection. The addition of the amino acid(s), for example methionine, arginine and combinations thereof may also optimise the preferential hydration/exclusion of the group B adenovirus. This parameter is thought to be of major importance in stabilising the group B adenovirus. Preferential interactions can be expressed in terms of preferential binding of the co-solvent (such as water) or its preferential exclusion (preferential hydration).

In one embodiment the formulation further comprises at least one amino acid, for example 1, 2, or 3 amino acids.

In one embodiment the at least one amino acid has a hydrophobic side chain, for example is selected from alanine, isoleucine, leucine, methionine, valine and combinations thereof.

In one embodiment the formulation further comprises methionine, for example 0.01-0.3 mM (0.01-0.2 mM), for example 0.01, 0.02, 0.03, 0.04, 0.05, 0.06, 0.07, 0.08, 0.09, 0.10, 0.12, 0.13, 0.14, 0.15, 0.16, 0.17, 0.18, 0.19, 0.20 mM such as 0.15 mM methionine. Alternatively, the methionine may be present at 0.25 mM in the formulation.

In one embodiment the formulation the at least one amino acid has a basic electronically charged side chain, for example is selected from arginine, histidine, lysine and combinations thereof.

In one embodiment, the formulation further comprises arginine, for example 1 to 20 mM (or 1 to 15 mM), for example 2 to 10 mM of arginine, such as 2, 2.5, 3, 3.5, 4, 4.5, 5, 5.5, 6, 6.5, 7, 7.5, 8, 8.5, 9, 9.5, or 10 mM arginine. In one embodiment the arginine in the formulation is in the range 10 to 20 mM, for example 10, 11, 12, 13, 14, 15, 16, 17, 18, 19 or 20 mM, such as 14, 15 or 16 mM. Advantageously, the addition of arginine to the formulation further enhances the stability of the adenoviruses, particularly during the first 12 months of storage.

In one embodiment, the formulation further comprises one or more of the following: meglumine buffer, Glycine buffer, TRIS buffer. These buffers were all shown to produce good stability when incorporated into the disclosed formulation.

In one embodiment, the formulation comprises meglumine buffer, for example at pH 8.0. Meglumine buffer is suitable for use in the pH range 8.0 to 10.5 such as 8.5 to 10.5.

In one embodiment the buffer is TRIS. TRIS is able to buffer in the range pH 7 to 9. In one embodiment the buffer does not comprise TRIS.

In one embodiment the buffer is glycine buffer, which is able to buffer in the range pH 8.6 to 10.6

The buffer must to be selected to match the pH, for example HEPES is only able to buffer up to pH 8.2. Other buffers disclosed herein may provide improved stability profiles for group B adenoviruses compared to HEPES. Thus, although HEPEs is commonly used for the storage of Group B adenoviruses such as EnAd, in one embodiment, the formulation does not comprise HEPES buffer.

In one embodiment the virus in the formulation according to the present disclosure encodes, 1, 2, 3 or 4 transgenes.

Definitions for Formula (I)

In one embodiment $B_X$ comprises a restriction site, for example 1, 2, 3 or 4 restriction sites, such as 1 or 2. In one embodiment $B_X$ comprises at least one transgene, for example 1 or 2 transgenes. In one embodiment $B_X$ comprises at least one transgene, for example 1 or 2 transgenes and one or more restriction sites, for example 2 or 3 restriction sites, in particular where the restriction sites sandwich a gene or the DNA sequence comprising the genes to allow it/them to be specifically excised from the genome and/or replaced. Alternatively, the restriction sites may sandwich each gene, for example when there are two transgenes three different restriction sites are required to ensure that the genes can be selectively excised and/or replaced. In one embodiment one or more, for example all the transgenes are in the form a transgene cassette.

In one embodiment $B_X$ does not comprise a restriction site. In one embodiment $B_X$ is a bond. In one embodiment Bx comprises or consists of one or more transgenes.

In one embodiment $B_Y$ comprises a restriction site, for example 1, 2, 3 or 4 restriction sites, such as 1 or 2. In one embodiment $B_Y$ comprises at least one transgene, for example 1 or 2 transgenes. In one embodiment $B_Y$ comprises at least one transgene, for example 1 or 2 transgenes and one or more restriction sites, for example 2 or 3 restriction sites, in particular where the restriction sites sandwich a gene or the DNA sequence comprising the genes to allow it/them to be specifically excised from the genome and/or replaced. Alternatively, the restriction sites may sandwich each gene, for example when there are two transgenes three different restriction sites are required to ensure that the genes can be selectively excised and/or replaced.

In one embodiment $B_Y$ does not comprise a restriction site. In one embodiment $B_Y$ is a bond. In one embodiment $B_Y$ comprises or consists of one or more transgenes.

In addition to minimising the size of the transgene cassette, employing an endogenous promoter in the virus may also be advantageous in a therapeutic context because the transgene is only expressed when the virus is replicating. This is in contrast to a constitutive exogenous promoter which will continually transcribe the transgene and may lead to an inappropriate concentration or localization of the encoded entity, such as the encoded polypeptide.

Alternatively, employing an exogenous promoter may be advantageous because it can strongly and constitutively express the encoded entity, which may be particularly useful in some situations, for example where the patient has very pervasive cancer. Hence, in one embodiment expression of the transgene is under the control of a CMV promoter.

In one embodiment, the transgene cassette further comprises a regulatory element independently selected from: a splice acceptor sequence, an internal ribosome entry sequence or a high self-cleavage efficiency 2A peptide, a Kozak sequence, and combinations thereof.

In one embodiment, the transgene cassette comprises a Kozak sequence is at the start of the protein coding sequence.

In one embodiment, the transgene cassette encodes a high self-cleavage efficiency 2A peptide.

In one embodiment, the transgene cassette further comprises a polyadenylation sequence.

In one embodiment, the transgene cassette further comprises a restriction site at the 3'end of the DNA sequence and/or at the 5'end of the DNA sequence.

DETAILED DESCRIPTION OF THE DISCLOSURE

The presently disclosed formulation has a alkaline pH, which is above physiological pH. The buffering of a given solution to a specific pH can be performed using routine techniques know in the art, for example including to an acid/base system comprising Tris, lysine, a strong acid (e.g. HCl) or a weak acid (e.g. acetic acid or maleic acid, a strong base (e.g. NaOH) or weak base (e.g. ammonia).

As used herein, buffer refers to a buffer suitable for suspending or storing group B adenoviruses, without negatively affecting the structural integrity of said group B adenoviruses or their ability to replicate for example. Most biological buffers in use today were developed by NE Good and his research team (Good et al. 1966, Good & Izawa 1972, Ferguson et al. 1980; “Good buffers”) and include N-substituted taurine or glycine buffers. Some commonly used biological buffers are listed below. This list is not exhaustive and other buffers will also be known to the skilled addressee.

In one embodiment, the disclosed formulation comprises one or more of the following buffers: 2-aminoethanesulfonic acid (AES) buffer, formate buffer (such as ammonium formate buffer, ammonium acetate buffer), 2-amino-2-methyl-1-propanol (AMP) buffer, 2-amino-2-methyl-1-propanediol (AMPD) buffer, N-(1,1-Dimethyl-2-hydroxyethyl)-3-amino-2-hydroxypropane sulfonic acid (AMPSO) buffer, bicine buffer, bis-tris-propane, boric acid buffer, 3-(cyclohexylamino)-2-hydroxy-1-propanesulfonic acid (CAPSO) buffer, N-Cyclohexyl-2-aminoethanesulfonic acid (CHES) buffer, 3-[4-(2-Hydroxyethyl)-1-piperazinyl]propanesulfonic acid (HEPPS) buffer, 1-methylpiperidine buffer, 4-(2-Hydroxyethyl)piperazine-1-(2-hydroxypropanesulfonic acid) (HEPPSO) buffer, glycylglycine buffer, piperazine-1,4-bis(2-hydroxypropanesulfonic acid) dihydrate or Piperazine-N,N'-bis(2-hydroxypropanesulfonic acid) (POPSO) buffer, [tris(hydroxymethyl)methylamino] propanesulfonic acid (TAPS) buffer, 3-[N-tris(hydroxylmethyl)-methylamino]-2-hydroxypropanesulfonic acid (TAPSO) buffer, triethanolamine buffer, 2-[tris(hydroxymethyl)-methylamino]-ethanesulfonic acid (TES) buffer, tricine buffer, meglumine buffer, glycine buffer (such as Gly-NaOH), TRIS buffer.

In one embodiment, the disclosed formulation comprises one or more of the following buffers: meglumine buffer, Gly-NaCl buffer, TRIS buffer.

Long term as used herein refers to a period of at least 6 months, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 months. In one embodiment, the disclosed formulation allows group B adenoviruses to be stably stored for at least 12 months, such as 12 months, 18 months and 24 months. Unless specified, long term storage generally refers to storage at 4° C.

In one embodiment the formulation is stored at a temperature in the range −1 to −95° C., for example −1 to −80° C., such as −1, −2, −3, −4, or −65, −66, −67, −68, −69, −70, −71, −72, −73, −74, −75, −77, −78, −79, −80, −81, −82, −83, −84, −85, −86, −87, −88, −89 or −90° C., in particular −80° C.

In one embodiment there is provided a liquid parenteral formulation (including a reconstituted formulation), for example for infusion or injection, for example of a replication capable oncolytic according to the present disclosure wherein the formulation provides a dose in the range of $1\times10^{10}$ to $1\times10^{14}$ viral particles per volume of dose.

In one embodiment the liquid formulations is provided as a concentrate, which requires dilution before administration to a patient.

In one embodiment the formulation is provided as a lyophilised formulation for reconstitution with an injectable liquid, such as water for injection, saline or glucose.

In one embodiment the formulation is provided as a liquid concentration, for dilution with liquid for injection, such as water for injection, saline, glucose or similar.

In one embodiment the formulation is manufactured as a liquid (is not lyophilised at any time), in particular in a final form, i.e. suitable for administration to a patient.

Parenteral formulation means a formulation designed not to be delivered through the GI tract. Typical parenteral delivery routes include injection, implantation or infusion. In one embodiment the formulation is provided in a form for bolus delivery.

In one embodiment the parenteral formulation is in the form of an injection. Injection includes intravenous, subcutaneous, intra-tumoral or intramuscular injection. Injection as employed herein means the insertion of liquid into the body via a syringe. In one embodiment the method of the present disclosure does not involve intra-tumoral injection.

In one embodiment the parenteral formulation is in the form of an infusion.

Infusion as employed herein means the administration of fluids by drip, infusion pump, syringe driver or equivalent device. In one embodiment the infusion is administered over a period in the range of 1.5 minutes to 120 minutes, such as about 3, 4, 5, 6, 7, 8, 9, 10, 11, 12, 13, 14, 15, 16, 17, 18, 19 20, 25, 30, 35, 40, 45, 50, 55, 60, 65, 70, 65, 80, 85, 90, 95, 100, 105, 110 or 115 minutes.

In one embodiment one dose of the formulation less than 100 mls, for example 30 mls, such as administered by a syringe driver.

In one embodiment the injection is administered as a slow injection, for example over a period of 1.5 to 30 minutes. Slow injection as employed herein is manual injection with syringe.

In one embodiment the formulation is for intravenous (i.v.) administration. This route is particularly effective for delivery of oncolytic virus because it allows rapid access to the majority of the organs and tissue and is particular useful for the treatment of metastases, for example established metastases especially those located in highly vascularised regions such as the liver and lungs.

Therapeutic formulations typically will be sterile and stable under the conditions of manufacture and storage. The composition can be formulated as a solution, microemulsion, liposome, or other parenteral formulation suitable for administration to a human.

Formulations according to the present disclosure may be formulated as a pre-filled device such as a syringe or vial, particular as a single dose.

The formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40. In dispersions the maintenance of the required particle size may be assisted by the presence of a surfactant. Examples of isotonic agents include sugars, polyalcohols such as mannitol, sorbitol, or sodium chloride in the composition.

In one embodiment parenteral formulations employed may comprise a sugar for example dextrose, mannose, sucrose or similar, a salt such as sodium chloride, magnesium chloride or potassium chloride and a combination of two or more the same.

In one embodiment the formulation according to the present disclosure does not comprise a sugar. Components of the buffer are not considered sugars, for the purpose of this disclosure.

In one embodiment the formulation of the present disclosure does not comprise a salt, such as sodium chloride. Reagents employed in the buffer are not considered salt for the purposes of the present disclosure.

In one embodiment the formulation of the present disclosure does not comprise a divalent cation, for example $CaCl_2$, and/or $MgCl_2$.

The formulation may also comprise a preservative such as EDTA. In one embodiment the formulation of the present disclosure does not contain EDTA.

In one embodiment the formulation according to the present disclosure does not comprise chlorobutanol.

In one embodiment the formulation of the disclosure does not comprise gelatin.

In one embodiment the formulations don't contain any ingredients which increase the immunogenicity of the group B adenovirus i.e. the formulations don't contain adjuvant(s).

In one embodiment the formulation will comprise purified oncolytic virus according to the present disclosure, for example $1\times10^{10}$ to $1\times10^{14}$ viral particles per dose, such as $1\times10^{10}$ to $1\times10^{12}$ viral particles per dose. In one embodiment the concentration of virus in the formulation is in the range $2\times10^{8}$ to $2\times10^{14}$ vp/ml, such as $2\times10^{12}$ vp/ml.

A thorough discussion of pharmaceutically acceptable carriers is available in Remington's Pharmaceutical Sciences (Mack Publishing Company, N.J. 1991).

The present disclosure also extends to liquid solutions or suspensions delivered intra-nasally, for example employing a device as disclosed in WO2009/068877 and US2004/0153033 both incorporated herein by reference.

Group B Adenovirus as employed will generally refer to a replication capable (including replication competent) adenovirus or replication deficient virus designated as a group B virus, for example Ad11, such as Ad11p including chimaeras thereof, such as EnAd, unless the context indicates otherwise. In some instances, it may be employed to refer only to replication competent viruses and this will be clear from the context.

Subgroup B (group B or type B) as employed herein refers to viruses with at least the fibre and hexon from a group B adenovirus, for example the whole capsid from a group B virus, such as substantially the whole genome from a group B virus. Subgroup B viruses include 3, 7, 11, 14, 16, 21, 34, 35, 50 and 55.

In one embodiment the virus of the disclosure, such as an oncolytic virus has an Ad11 hexon, such as an A11p hexon. In one embodiment the virus of the disclosure, such as an oncolytic virus has a subgroup B fibre. In one the virus of the disclosure, such as an oncolytic virus has an Ad11 fibre, such as an A11p fibre. In one embodiment the virus of the disclosure, such as an oncolytic virus has fibre and hexon proteins from the same serotype, for example a subgroup B adenovirus, such as Ad11, in particular Ad11p.

In one embodiment the virus of the disclosure, such as an oncolytic virus has fibre, hexon and penton proteins from the same serotype, for example Ad11, in particular Ad11p, for example found at positions 30811-31788, 18254-21100 and 13682-15367 of the genomic sequence of the latter.

Enadenotucirev (EnAd) is a chimeric oncolytic adenovirus, formerly known as ColoAd1 (WO2005/118825), with fibre, penton and hexon from Ad11p, hence it is a group B virus. It has a chimeric E2B region, which comprises DNA from Ad11p and Ad3. Almost all of the E3 region and part of the E4 region is deleted in EnAd.

E3 as employed herein refers to the DNA sequence encoding part or all of an adenovirus E3 region (i.e. protein/polypeptide), it may be mutated such that the protein encoded by the E3 gene has conservative or non-conservative amino acid changes, such that it has the same function as wild-type (the corresponding unmutated protein); increased function in comparison to wild-type protein; decreased function, such as no function in comparison to wild-type protein or has a new function in comparison to wild-type protein or a combination of the same, as appropriate. Where part of the E3 region is deleted (partly deleted in the E3 region) includes where 1 to 99% of the E3 region is deleted, such as 2, 3, 4, 5, 6, 7, 8, 9, 10, 15, 20, 25, 30, 35, 40, 45, 50, 55, 60, 65, 70, 75, 80, 85, 90, 91, 92, 93, 94 95, 96, 97 or 98% deleted, for example in a coding and/or non-coding region of the gene.

E4 as employed herein refers to the DNA sequence encoding an adenovirus E4 region (i.e. polypeptide/protein region), which may be mutated such that the protein encoded by the E4 gene has conservative or non-conservative amino acid changes, and has the same function as wild-type (the corresponding non-mutated protein); increased function in comparison to wild-type protein; decreased function, such as no function in comparison to wild-type protein or has a new function in comparison to wild-type protein or a combination of the same as appropriate.

The E4 region may have some function or functions relevant to viral replication and thus modifications, such as deletion of the E4 region may impact on a virus life-cycle and replication, for example such that a packaging cell may be required for replication.

In one embodiment E4 has the E4ORF4 region deleted.

"Derived from" as employed herein refers to, for example where a DNA fragment is taken from an adenovirus or corresponds to a sequence originally found in an adenovirus. This language is not intended to limit how the sequence was obtained, for example a sequence employed in a virus according to the present disclosure may be synthesised.

In one embodiment the derivative has 100% sequence identity over its full length to the original DNA sequence.

In one embodiment the derivative has 95, 96, 97, 98 or 99% identity or similarity to the original DNA sequence.

In one embodiment the derivative hybridises under stringent conditions to the original DNA sequence.

As used herein, "stringency" typically occurs in a range from about Tm (melting temperature) −50° C. (5° below the Tm of the probe) to about 20° C. to 25° C. below Tm.• As will be understood by those of skill in the art, a stringent hybridization can be used to identify or detect identical polynucleotide sequences or to identify or detect similar or related polynucleotide sequences. As herein used, the term "stringent conditions" means hybridization will generally occur if there is at least 95%, such as at least 97% identity between the sequences.

As used herein, "hybridization" as used herein, shall include "any process by which a polynucleotide strand joins with a complementary strand through base pairing" (Coombs, J., *Dictionary of Biotechnology*, Stockton Press, New York, N.Y., 1994).

Oncolytic viruses are those which preferentially infect cancer cells and hasten cell death, for example by lysis of same, or selectively replicate in the cancer cells. Viruses which preferentially infect cancer cells are viruses which show a higher rate of infecting cancer cells when compared to normal healthy cells.

Viruses which selectively replicate in cancer cells are those which require a gene or protein which is upregulated in a cancer cell to replicate, such as a p53 gene.

The E2B region is a known region in group B adenoviruses and represents about 18% of the viral genome. It is thought to encode protein IVa2, DNA polymerase and terminal protein. In the Slobitski strain of Ad11 (referred to as Ad11p) these proteins are encoded at positions 5588-3964, 8435-5067 and 10342-8438 respectively in the genomic sequence and the E2B region runs from 10342-3950. The exact position of the E2B region may change in other serotypes but the function is conserved in all human adenovirus genomes examined to date as they all have the same general organisation.

Replication capable as employed herein refers to a virus capable of replicating in vivo, including a virus with replication dependent on an upregulated gene in a diseased cell, such as p53, and replication competent viruses.

In one embodiment the virus is replication competent. Replication competent virus as employed herein refers to a virus that is capable of replication without the assistance of a complementary cell line encoding an essential viral protein, such as that encoded by the E1 region (also referred to as a packaging cell line) and a virus capable of replicating without the assistance of a helper virus.

Viral vectors as employed herein are replication deficient. Replication deficient viruses of the present disclosure require a packaging cell line to replicate. Packaging cell lines contain a gene or genes to complement those which are deficient in the virus.

In one embodiment the present disclosure provides a process of preparing a pharmaceutical formulation comprising the step of mixing a group B adenovirus (such as a replication competent group B virus) with 15 to 25% v/v of glycerol, 0.1 to 1.5% v/v of ethanol, a buffer (wherein the % v/v is the final formulation volume) and if required adjusting the pH to be in the range 8.0 to 9.5, for example 8.0 to 9.5 (or 8.5 to 9.5), such as 8.0 to 8.5 (or 8.5 to 9.)

In one embodiment the process further comprises the addition of 0.01 to 0.3 mM, for example 0.01 to 0.25 mM (or 0.01 to 2 mM), such as 0.25 mM (or 0.15 mM) methionine.

In one embodiment the formulation comprises a virus sequence disclosed in the associated sequence listing filed herewith.

Treatment

The patient recipient of the formulation according to the present disclosure, may be a human or animal, such as a domestic animal. In one embodiment the patient is a human, such as an adult human.

The formulation of present disclosure is suitable for formulation of replication capable (including replication competent) group B adenoviruses and replication deficient group B adenoviral vectors, for therapeutic and diagnostic applications, for example for gene therapy applications, vaccines, cancer treatment and the like.

In a further aspect the present disclosure extends to a formulation as described herein for use in treatment, in particular for the treatment of cancer.

In one embodiment the method of treatment is for use in the treatment of a tumour.

Tumour as employed herein is intended to refer to an abnormal mass of tissue that results from excessive cell division that is uncontrolled and progressive, also called a neoplasm. Tumours may be either benign (not cancerous) or malignant. Tumour encompasses all forms of cancer and metastases. In one embodiment the tumour is cancerous.

In one embodiment the tumour is a solid tumour. The solid tumour may be localised or metastasised.

In one embodiment the tumour is of epithelial origin.

In one embodiment the tumour is a malignancy, such as colorectal cancer, hepatoma, prostate cancer, pancreatic cancer, breast cancer, ovarian cancer, thyroid cancer, renal cancer, bladder cancer, head and neck cancer or lung cancer.

In one embodiment the tumour is a colorectal malignancy.

Malignancy as employed herein refers to cancerous cells.

In one embodiment the oncolytic adenovirus is employed in the treatment or prevention of metastasis.

In one embodiment the formulation herein is employed in the treatment of drug resistant cancers.

In one embodiment the virus is administered in combination with the administration of a further cancer treatment or therapy.

In one embodiment there is provided a formulation according to the present disclosure for use in the manufacture of a medicament for the treatment of cancer, for example a cancer described above.

In a further aspect there is provide a method of treating cancer comprising administering a therapeutically effective amount of a formulation according to the present disclosure to a patient in need thereof, for example a human patient.

In one embodiment the formulation herein is administered in combination with another therapy.

"In combination" as employed herein is intended to encompass where the formulation herein is administered before, concurrently and/or post cancer treatment or therapy. However, generally the treatment regimens for the combination therapy will generally overlap.

Cancer therapy includes surgery, radiation therapy, targeted therapy and/or chemotherapy.

Cancer treatment as employed herein also refers to treatment with a therapeutic compound or biological agent, for example an antibody intended to treat the cancer and/or maintenance therapy thereof.

In one embodiment the cancer treatment is selected from any other anti-cancer therapy including a chemotherapeutic agent; a targeted anticancer agent, such as an antibody drug conjugate; radiotherapy, radio-isotope therapy or any combination thereof.

In one embodiment the formulation of the present disclosure may be used as a pre-treatment to the therapy, such as a surgery (neoadjuvant therapy), to shrink the tumour, to treat metastasis and/or prevent metastasis or further metastasis. The formulation may be used after the therapy, such as a surgery (adjuvant therapy), to treat metastasis and/or prevent metastasis or further metastasis.

In one embodiment a formulation of the present disclosure is employed in maintenance therapy.

In one embodiment the formulation according to the present disclosure is administered in combination with, for example concurrently with, a cancer therapy.

Concurrently as employed herein is the administration of the additional cancer treatment at the same time or approximately the same time as the formulation. The treatment may be contained within the same formulation or administered as a separate formulation.

In one embodiment the virus is administered in combination, for example concurrently, with the administration of a chemotherapeutic agent.

Chemotherapeutic agent as employed herein is intended to refer to specific antineoplastic chemical agents or drugs that are selectively destructive to malignant cells and tissues. For example, alkylating agents, antimetabolites, anthracyclines, plant alkaloids, topoisomerase inhibitors, and other antitumour agents. Examples of specific chemotherapeutic agents include doxorubicin, 5-fluorouracil (5-FU), paclitaxel, capecitabine, irinotecan, and platins, such as cisplatin and oxaliplatin. The dose may be chosen by the practitioner based on the nature of the cancer being treated.

Combination Therapies & Chemotherapeutic Agents

The formulation of the present disclosure may be employed in combination with a further cancer therapy, for example chemotherapy.

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, topoisomerase inhibitors, parp inhibitors and other anti-tumour agents. Selectively in this context is used loosely because of course many of these agents have serious side effects.

The preferred dose may be chosen by the practitioner, based on the nature of the cancer being treated.

Examples of alkylating agents, which may be employed in the method of the present disclosure include an alkylating agent nitrogen mustards, nitrosoureas, tetrazines, aziridines, platins and derivatives, and non-classical alkylating agents.

Example a platinum containing chemotherapeutic agent (also referred to as platins), such as cisplatin, carboplatin, oxaliplatin, satraplatin, picoplatin, nedaplatin, triplatin and lipoplatin (a liposomal version of cisplatin), in particular cisplatin, carboplatin and oxaliplatin.

The dose for cisplatin ranges from about 20 to about 270 $mg/m^2$ depending on the exact cancer. Often the dose is in the range about 70 to about 100 $mg/m^2$.

Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed (Tomudex®) hydrochloride, cladribine and 6-azauracil.

Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin currently used only to treat bladder cancer and mitoxantrone an anthracycline analog, in particular doxorubicin.

Examples of anti-microtubule agents, which may be employed in the method of the present disclosure, include vinca alkaloids and taxanes.

Vinca alkaloids include completely natural chemicals for example vincristine and vinblastine and also semi-synthetic vinca alkaloids, for example vinorelbine, vindesine, and vinflunine.

Taxanes include paclitaxel, docetaxel, Abraxane®, cabazitaxel and derivatives of thereof. Derivatives of taxanes as employed herein includes reformulations of taxanes like Taxol, for example in a micellular formulations, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, innotecan and indometacin. Type II inhibitors include genistein and ICRF 193 which has the following structure:

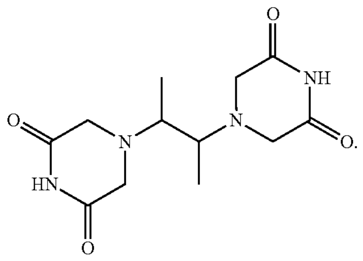 [SMILES: CC(C(C)N1CC(=O)NC(=O)C1)N1CC(=O)NC(=O)C1]

Type II poisons include amsacrine, etoposide, etoposide phosphate, teniposide and doxorubicin and fluoroquinolones.

In one embodiment a combination of chemotherapeutic agents employed is, for example a platin and 5-FU or a prodrug thereof, for example cisplatin or oxaplatin and capecitabine or gemcitabine, such as FOLFOX.

In one embodiment the chemotherapy comprises a combination of chemotherapy agents, in particular cytotoxic chemotherapeutic agents.

In one embodiment the chemotherapy combination comprises a platin, such as cisplatin and fluorouracil or capecitabine.

In one embodiment the chemotherapy combination in capecitabine and oxaliplatin (Xelox).

In one embodiment the chemotherapy is a combination of folinic acid and 5-FU, optionally in combination with oxaliplatin.

In one embodiment the chemotherapy is a combination of folinic acid, 5-FU and irinotecan (FOLFIRI), optionally in combination with oxaliplatin (FOLFIRINOX). The regimen consists of: irinotecan (180 mg/$m^2$ IV over 90 minutes) concurrently with folinic acid (400 mg/$m^2$ [or 2×250 mg/$m^2$] IV over 120 minutes); followed by fluorouracil (400-500 mg/$m^2$ IV bolus) then fluorouracil (2400-3000 mg/$m^2$ intravenous infusion over 46 hours). This cycle is typically repeated every two weeks. The dosages shown above may vary from cycle to cycle.

In one embodiment the chemotherapy combination employs a microtubule inhibitor, for example vincristine sulphate, epothilone A, N-[2-[(4-Hydroxyphenyl)amino]-3-pyridinyl]-4-methoxybenzenesulfonamide (ABT-751), a Taxol derived chemotherapeutic agent, for example paclitaxel, abraxane, or docetaxel or a combination thereof.

In one embodiment the combination employs an mTor inhibitor. Examples of mTor inhibitors include: everolimus (RAD001), WYE-354, KU-0063794, papamycin (Sirolimus), Temsirolimus, Deforolimus (MK-8669), AZD8055 and BEZ235 (NVP-BEZ235).

In one embodiment the combination employs a MEK inhibitor. Examples of MEK inhibitors include: AS703026, CI-1040 (PD184352), AZD6244 (Selumetinib), PD318088, PD0325901, AZD8330, PD98059, U0126-EtOH, BIX 02189 or BIX 02188.

In one embodiment the combination employs an AKT inhibitor. Examples of AKT inhibitors include: MK-2206 and AT7867.

In one embodiment the combination employs an aurora kinase inhibitor. Examples of aurora kinase inhibitors include: Aurora A Inhibitor I, VX-680, AZD1152-HQPA (Barasertib), SNS-314 Mesylate, PHA-680632, ZM-447439, CCT129202 and Hesperadin.

In one embodiment the combination employs a p38 inhibitor, for example as disclosed in WO2010/038086, such as N-[4-({4-[3-(3-tert-Butyl-1-p-tolyl-1H-pyrazol-5-yl) ureido]naphthalen-1-yloxy}methyl)pyridin-2-yl]-2-methoxyacetamide.

In one embodiment the combination employs a pi3K inhibitor, for example selected from dactolisib, pictilisib, LY294002, idelalisib, buparlisib, autophinib, serabelisib, IP1-549, SF2534, GDC-0326, SAR405, TGR-1202, VPS34, GSK2269557, 740 Y-P, PI-103, NU7441, TGX-221, IC-87114, wortmannin, XL147 analogue, ZSTK474, alpelisib, AS-605240, PIK-75, 3-methyladenine, A66, voxtalisib, PIK-93, AZD6482, PF-04691502, apitolisib, GSK105965, duvelisib, TG100-115, AS-252424, BGT226, CUDU-907, PIK-294, AS-604850, GSK2636771, copanlisib, YM201636, CH5132799, CAY10505, PIK-293, TG100713, VS-5584, taselisib, CZC24832, AMG319, GSK2292767, GDC-0084, HS-173, quercetin, voxtalisib, GNE-317, LY3023414, VPS34-IN1, PIK-III, PI-3065, pilaralisib, AZD8835, PF-4989216 and AZD8186.

In one embodiment the combination employs a Bcl-2 inhibitor. Examples of Bcl-2 inhibitors include: obatoclax mesylate, ABT-737, ABT-263 (navitoclax) and TW-37.

In one embodiment the chemotherapy combination comprises an antimetabolite such as capecitabine (Xeloda®), fludarabine phosphate, fludarabine (Fludara), decitabine, raltitrexed (Tomudex®), gemcitabine hydrochloride and cladribine.

In one embodiment the combination comprises ganciclovir, which may assist in controlling immune responses and/or tumour vasculation.

In one embodiment the combination comprises a PARP inhibitor.

In one embodiment the therapeutic agent is ganciclovir, which may assist in controlling immune responses and/or tumour vascularisation.

In one embodiment one or more therapies employed in the method herein are metronomic, that is a continuous or frequent treatment with low doses of anticancer drugs, often given concomitant with other methods of therapy.

Subgroup B oncolytic adenoviruses (in particular Ad11 and those derived therefrom, such as EnAd) may be particularly synergistic with chemotherapeutics because they seem to have a mechanism of action that is largely independent of apoptosis, killing cancer cells by a predominantly necrolytic mechanism. Moreover, the immunosuppression that occurs during chemotherapy may allow the oncolytic virus to function with greater efficiency.

Therapeutic dose as employed herein refers to the amount of virus, such as oncolytic adenovirus that is suitable for achieving the intended therapeutic effect when employed in a suitable treatment regimen, for example ameliorates symptoms or conditions of a disease, in particular without eliciting dose limiting side effects. A dose may be considered a therapeutic dose in the treatment of cancer or metastases when the number of viral particles may be sufficient to result in the following: tumour or metastatic growth is slowed or stopped, or the tumour or metastasis is found to shrink in size, and/or the life span of the patient is extended. Suitable therapeutic doses are generally a balance between therapeutic effect and tolerable toxicity, for example where the side-effect and toxicity are tolerable given the benefit achieved by the therapy.

In one embodiment there is provided systemically administering multiple doses of a parenteral formulation of an oncolytic adenovirus according to the present disclosure in a single treatment cycle, for example wherein the total dose given in each administration is in the range of $1\times10^{10}$ to $1\times10^{14}$ viral particles per dose.

In one embodiment one or more doses (for example each dose) of virus or composition comprising the same is administered such that the rate of viral particle delivery is in the range of $2\times10^{10}$ particles per minute to $2\times10^{12}$ particles per minute.

In one embodiment a virus or therapeutic construct according to the present disclosure (including a formulation comprising same) is administered weekly, for example on week 1 the dose is administered on day 1, 3, 5, followed by one dose each subsequent week.

In one embodiment a virus or therapeutic construct according to the present disclosure (including a formulation comprising same) is administered bi-weekly or tri-weekly, for example is administered in week 1 one on days 1, 3 and 5, and on week 2 or 3 is also administered on days 1, 3 and 5 thereof. This dosing regimen may be repeated as many times as appropriate.

In one embodiment a formulation according to the present disclosure (including a formulation comprising same) is administered monthly, for example in a treatment cycle or as maintenance therapy.

In one embodiment the viruses and constructs of the present disclosure are prepared by recombinant techniques. The skilled person will appreciate that the armed adenovirus genome can be manufactured by other technical means, including entirely synthesising the genome or a plasmid comprising part of all of the genome. The skilled person will appreciate that in the event of synthesising the genome the region of insertion may not comprise the restriction site nucleotides as the latter are artefacts following insertion of genes using cloning methods.

In one embodiment the armed adenovirus genome is entirely synthetically manufactured.

In the context of this specification "comprising" is to be interpreted as "including".

Embodiments of the invention comprising certain features/elements are also intended to extend to alternative embodiments "consisting" or "consisting essentially" of the relevant elements/features.

Where technically appropriate, embodiments of the invention may be combined. Technical references such as patents and applications are incorporated herein by reference.

Any embodiments specifically and explicitly recited herein may form the basis of a disclaimer either alone or in combination with one or more further embodiments.

Heading herein are employed to divide the document into sections and are not intended to be used to construe the meaning of the disclosure provided herein.

The present application claims priority from GB 1801614.7, filed 31 Jan. 2018, and incorporated herein by reference. The priority application may be employed as the basis for correction to the present specification.

The present invention is further described by way of illustration only in the following examples.

BRIEF DESCRIPTION OF THE FIGURES

FIG. 1 shows results of experiments comparing the stability of group B adenoviruses in different buffers across a range of different pH values. (A) stability of adenoviruses stored at 2-8 for 20 months (B) stability of group B adenoviruses stored at 25° C. for 8 weeks.

FIG. 2 shows the results of experiments to determine the effect of glycerol on the stability of group B adenoviruses. (A) graphs show stability of group B adenoviruses at week 0, week 7 and week 17 across a range of different glycerol concentrations ranging from 8 to 20%. (B) graph showing role of glycerol in polydispersity over 7 weeks. (C) graph showing % change in concentration of group B adenoviruses in formulations containing 0%, 10% and 20% glycerol as measured by HPLC assay.

FIG. 3 shows results of experiments to ascertain ethanol/arginine/methionine/polysorbate contribute to stability of group B adenoviruses. (A) graph showing potency of a group B adenovirus over time for different buffers. (B) graph showing concentration of a group B adenoviruses over time for different buffers. (C) graph showing concentration of a control formulation comprising glycerol, HEPES buffer, ethanol, arginine, methionine and polysorbate over time.

FIG. 7 shows the relative retention times of Ad5 (a group C virus) and Ad11 (a group B virus) analysed by anion exchange chromatography.

FIG. 8C shows oncolytic relative potency analysis (20% glycerol, 1.4% ethanol, 15 mM arginine, 0.25 mM methionine).

FIG. 8D shows virus concentration by AEX-HPLC (20% glycerol, 1.4% ethanol, 15 mM arginine, 0.25 mM methionine)

SEQUENCES

Figure 4:
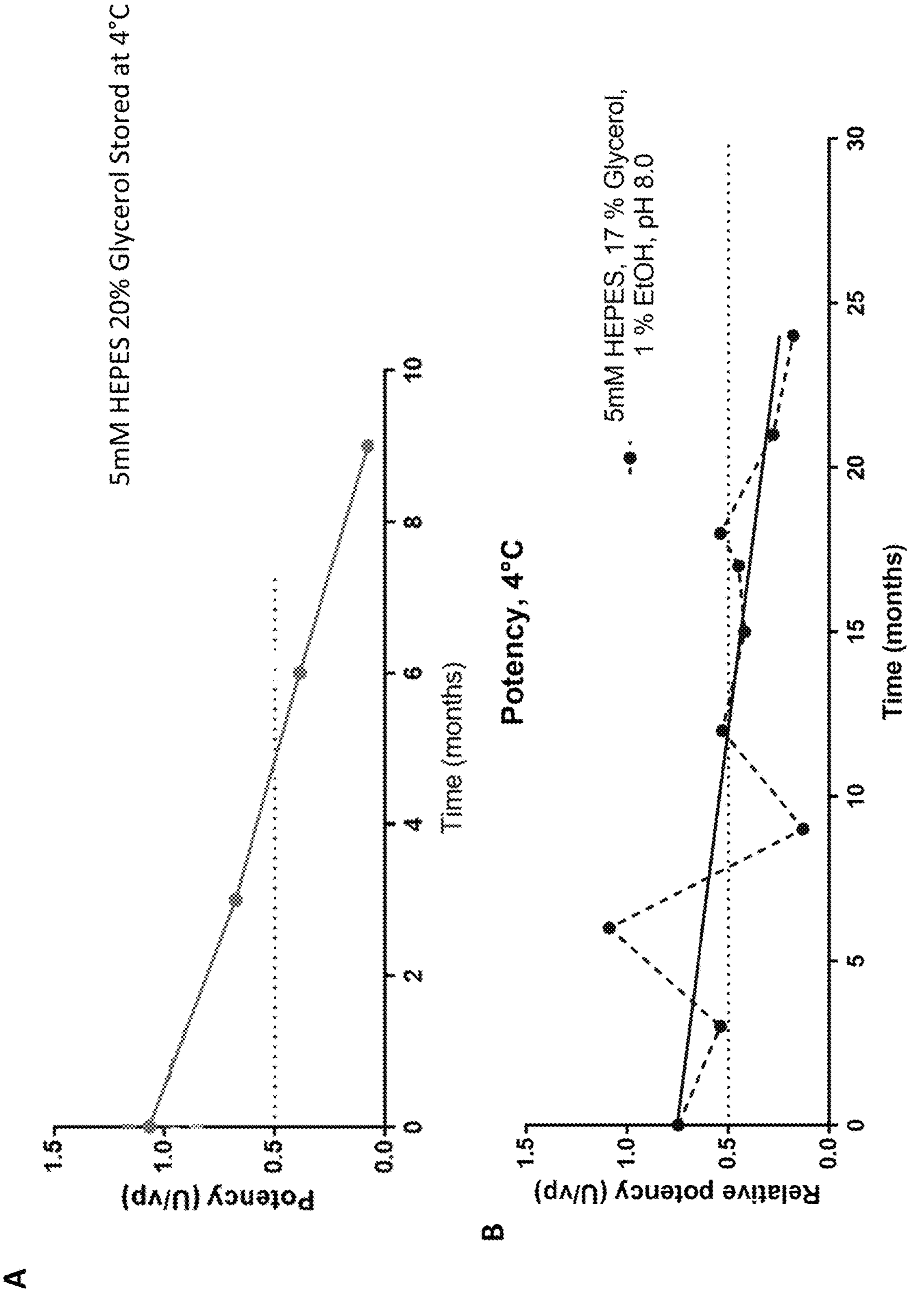
FIG. 4 shows results of experiments showing impact of ethanol, arginine and methionine on potency of adenoviruses during long term storage at 4° C. (A) shows the potency of group B adenovirus in 5 mM HEPES with 20% glycerol (B) graph showing effect on relative potency when ethanol is included in formulation. (C) graph showing effect on relative potency when ethanol and methionine are included in formulation. (D) graph showing effect on relative potency when ethanol, methionine and arginine are included in formulation. (E) graph showing concentration of adenoviruses over time for formulations tested in FIGS. 4B-4D.
Figure 4:
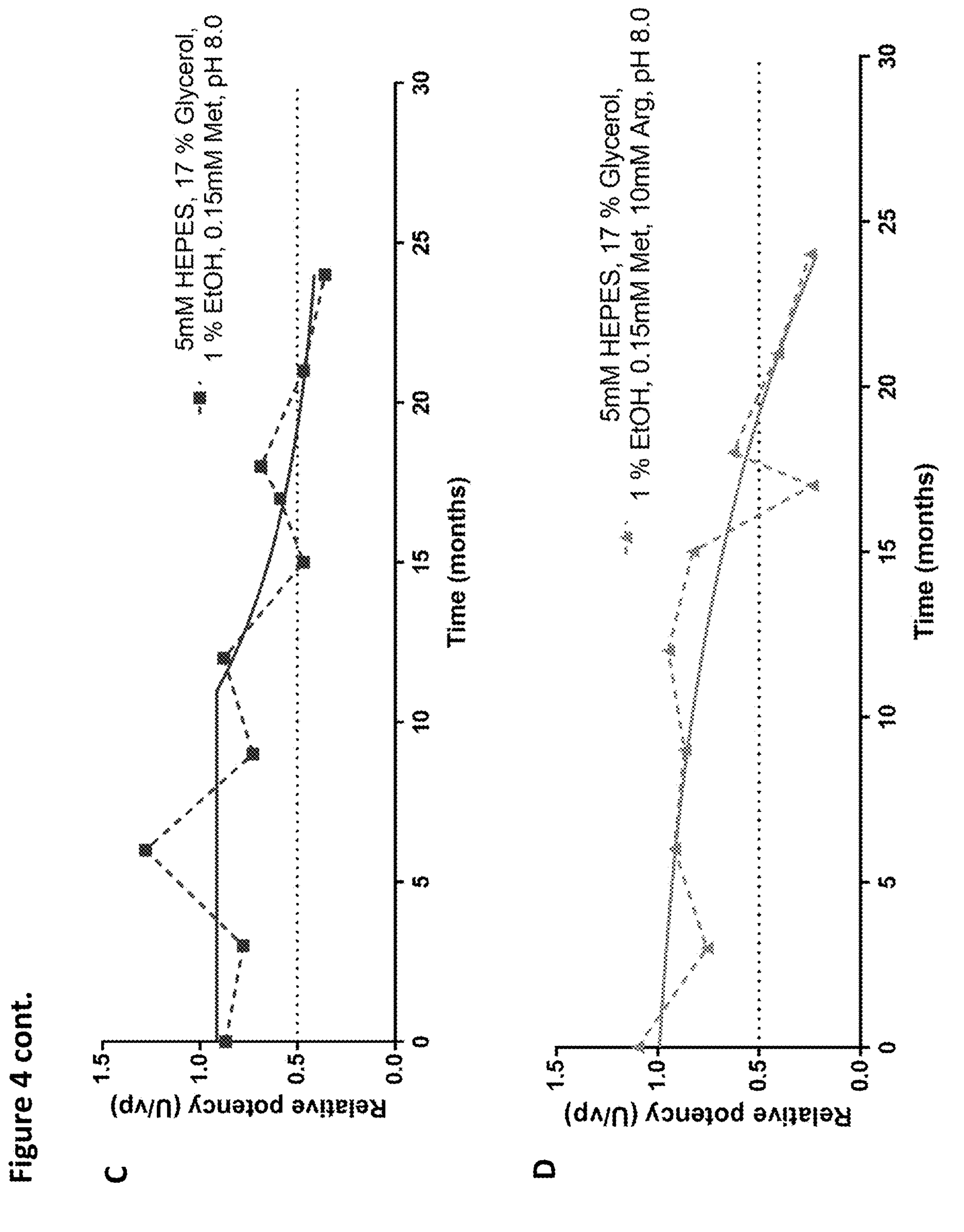
Figure 4:
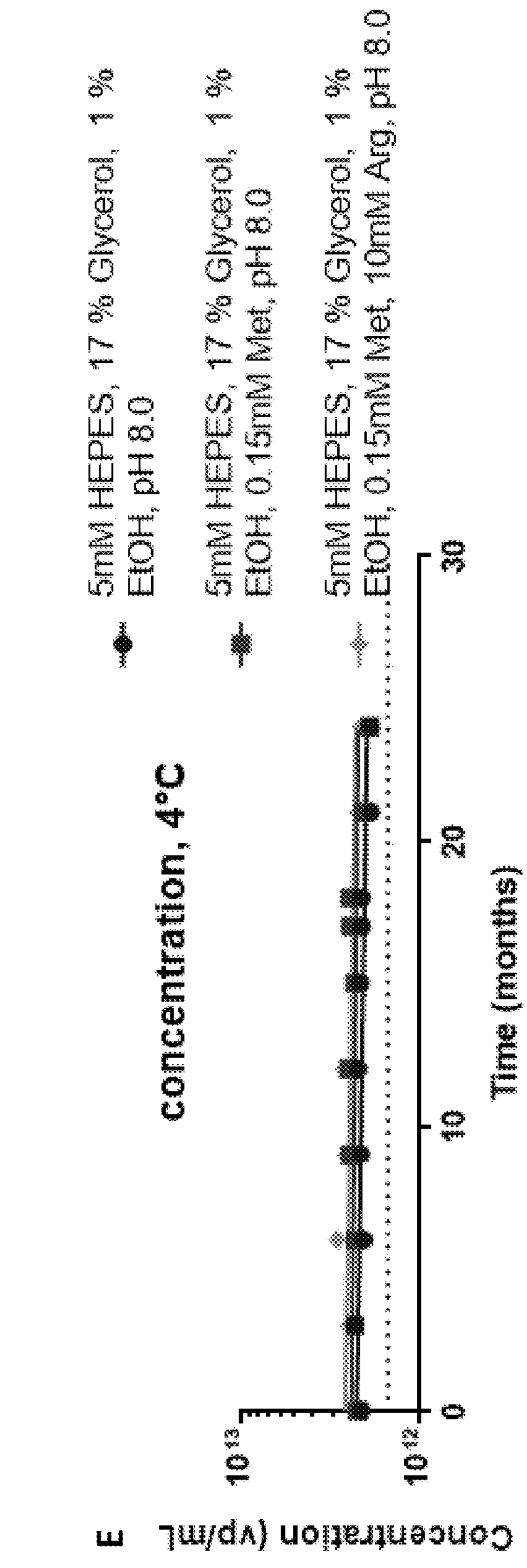

SEQ ID NO: 1 Splice Acceptor (SA); SEQ ID NO: 2 Branched Splice Acceptor (BSA); SEQ ID NO: 3

Internal Ribosome Entry sequence (IRES); SEQ ID NO: 4 Polyadenylation sequence SEQ ID NO: 5 BX DNA sequence corresponding to and including bp 28166-28366 of the EnAd genome; SEQ ID NO: 6 BY DNA sequence corresponding to and including bp 29345-29379 of the EnAd genome; SEQ ID NO: 7 Leader Sequence; SEQ ID NO: 8 Leader Sequence; SEQ ID NO: 9

P2A peptide; SEQ ID NO: 10 F2A peptide; SEQ ID NO: 11 E2A peptide; SEQ ID NO: 12 2A peptide; SEQ ID NO: 13 EnAd genome; SEQ ID NO: 14 NG-73 virus Genome Sequence; SEQ ID NO: 15 NG-74 virus Genome Sequence; SEQ ID NO: 16 NG-76 virus Genome Sequence; SEQ ID NO: 17 NG-77 virus Genome Sequence; SEQ ID NO: 18 NG-78 virus genome sequence SEQ ID NO: 19 NG-92 virus genome sequence; SEQ ID NO: 20 NG-95 virus genome sequence; SEQ ID NO: 21 NG-96 virus genome sequence; SEQ ID NO: 22 NG-97 virus genome sequence; SEQ ID NO: 23 NG-134 virus genome sequence; SEQ ID NO: 24 NG-135 virus genome sequence; SEQ ID NO: 25 NG-139 virus genome sequence consisting of a transgene cassette that encodes the cytokine, TNFa, inserted in the region BY; SEQ ID NO: 26 A virus genome sequence consisting of a transgene cassette that encodes an anti-VEGF full length antibody inserted in the region BY. The transgene cassette contains a SSA, ab heavy chain sequence with 5' leader, a SSA, and ab light chain sequence; SEQ ID NO: 27 A virus genome sequence consisting of a transgene cassette that encodes an anti-VEGF full length antibody inserted in the region BY; SEQ ID NO: 28 NG-165 virus genome sequence consisting of a transgene cassette encoding an anti-VEGF full length antibody inserted into the region BY; SEQ ID NO: 29 NG-167 virus genome sequence consisting of a transgene cassette that encodes an anti-VEGF ScFv with a C-terminal His6 tag, inserted in the region BY; SEQ ID NO: 30 NG-177 virus genome sequence consisting of a transgene cassette encoding an anti-PD-L1 full length antibody inserted into the region BY; SEQ ID NO: 31 NG-185 virus genome sequence consisting of the EnAd genome with unique restriction sites inserted into the BX and BY regions; SEQ ID NO: 32 NG-190 virus genome sequence consisting of a transgene cassette encoding an anti-PD-L1 full length antibody inserted into the region BY; SEQ ID NO: 33 NG-217 virus genome sequence consisting of a transgene cassette that encodes the tumour associated antigen, NY-ESO-1, inserted in the region BY; SEQ ID NO: 34 NG-220 virus genome sequence consisting of a transgene cassette that encodes the tumour associated antigen, NY-ESO-1, inserted in the region BY; SEQ ID NO: 35 NG-221 virus genome sequence consisting of the EnAd genome with a transgene cassette that encodes an anti-PD-L1 ScFv with a C-terminal His6 tag, inserted in the region BY; SEQ ID NO: 36 NG-242 virus genome sequence consisting of a transgene cassette encoding an anti-CTLA-4 full length antibody inserted into the region BY; SEQ ID NO: 37 NG-257 virus genome sequence comprising the EnAd genome with a transgene cassette encoding an anti-VEGF ScFv inserted into the region BX; SEQ ID NO: 38 NG258 virus genome sequence consisting of a transgene cassette encoding an anti-VEGF full length antibody inserted into the region BY; SEQ ID NO: 39 NG-272 virus genome sequence comprising the EnAd genome with a transgene cassette encoding an anti-VEGF ScFv and an anti-PD-L1 ScFv inserted into the region BY; SEQ ID NO: 40 NG-280 virus genome sequence consisting of a transgene cassette encoding the sodium iodide symporter (NIS) inserted into the region BY; SEQ ID NO: 41 NG-281 virus genome sequence comprising the EnAd genome with a transgene cassette encoding an anti-VEGF ScFv inserted into the region Bx and a second transgene cassette encoding an anti-PD-L1 ScFv inserted into the region BY; SEQ ID NO: 42 NG-330 virus genome sequence comprising the EnAd genome with a transgene cassette that encodes the T lymphocyte activation antigen, CD80, inserted in the region BY. The transgene cassette contains a 5' SSA, human CD80 cDNA sequence and a 3' poly(A) sequence; SEQ ID NO: 43 NG-343 virus genome sequence comprising the EnAd genome with a transgene cassette that encodes IFNα, and CD80, inserted in the region BY. The transgene cassette contains a 5' SSA, IFNα cDNA sequence, P2A peptide, CD80 cDNA sequence and a 3' poly(A) sequence; SEQ ID NO: 44 NG-641 genome; SEQ ID NO: 45 NG-345 virus genome sequence comprising the EnAd genome with a transgene cassette that encodes Flt3 Ligand, MIP1α and IFNα, inserted in the region BY. The transgene cassette contains a 5' SSA, Flt3 Ligand cDNA sequence, P2A peptide sequence, MIP1α cDNA sequence, T2A peptide sequence, IFNα cDNA sequence and a 3' poly(A) sequence; SEQ ID NO: 46 NG-346 virus genome sequence comprising the EnAd genome with a transgene cassette that encodes Flt3 Ligand, MIP1α and CD80, inserted in the region BY. The transgene cassette contains a 5' SSA, Flt3 Ligand cDNA sequence, P2A peptide sequence, MIP1α cDNA sequence, T2A peptide sequence, CD80 cDNA sequence and a 3' poly(A) sequence; SEQ ID NO: 47 NG-347 virus genome sequence comprising the EnAd genome with a transgene cassette that encodes IFNα, MIP1α and CD80, inserted in the region BY. The transgene cassette contains a 5' SSA, IFNα cDNA sequence, P2A peptide sequence, MIP1α cDNA sequence, T2A peptide sequence, CD80 cDNA sequence and a 3' poly(A) sequence; SEQ ID NO: 48 NG-348 virus genome sequence comprising the EnAd genome with a transgene cassette that encodes a membrane-anchored chimeric form of the single chain Fv anti-human CD3e and the T lymphocyte activation antigen, CD80 inserted in the region BY. The transgene cassette contains a 5' SSA, membrane-anchored anti-$CD3_ε$ cDNA sequence, P2A peptide, human CD80 cDNA sequence and a 3' poly(A) sequence; SEQ ID NO: 49 NG-348A virus genome sequence comprising the EnAd genome with a transgene cassette that encodes a membrane-anchored chimeric form of the single chain Fv anti-human CD3e with C-terminal V5 tag and the T lymphocyte activation antigen, CD80 inserted in the region BY. The transgene cassette contains a 5' SSA, membrane-anchored anti-CD3ε cDNA sequence, V5 tag, P2A peptide, human CD80 cDNA sequence and a 3' poly(A) sequence; SEQ ID NO: 50 NG-350A genome sequence; SEQ ID NO: 51 NG-420 virus genome sequence comprising the EnAd genome with a transgene cassette that encodes a membrane-anchored chimeric form of the single chain Fv anti-human CD3e inserted in the region BY. The transgene cassette contains a 5' SSA, membrane-anchored anti-CD3ε cDNA sequence and a 3' poly(A) sequence; SEQ ID NO: 52 NG-420A virus genome sequence comprising the EnAd genome with a transgene cassette that encodes a membrane-anchored chimeric form of the single chain Fv anti-human CD3e and a C-terminal V5 tag, inserted in the region BY. The transgene cassette contains a 5' SSA, membrane-anchored anti-CD3ε cDNA sequence, V5 tag sequence and a 3' poly(A) sequence; SEQ ID NO: 53 NG-601 (EnAd-CMV-EpCAMBiTE); SEQ ID NO: 54 NG-602 (EnAd-SA-EpCAMBiTE); SEQ ID NO: 55 NG-605 (EnAd-CMV-FAPBiTE); SEQ ID NO: 56 NG-606 (EnAd-SA-FAPBiTE); SEQ ID NO: 57 NG-611 genome; SEQ ID NO: 58 NG-612 genome; SEQ ID NO: 59 NG-613 genome; SEQ ID NO: 60 NG-614 genome; SEQ ID NO: 61 NG-615 genome; SEQ ID NO: 62 NG-616 genome; SEQ ID NO: 63 NG-617 genome; SEQ ID NO: 64 NG-618 genome; SEQ ID NO: 65 NG-640 Genome.

EXAMPLES

Example 1—Testing Influence of pH on Stability of Adenoviral Formulations

An experiment was conducted to determine the influence of pH on the stability of group B adenoviral formulations. Different buffers were tested: carbonate/bicarbonate, diethanolamine, Gly-NaCl, HEPEs, meglumine, sodium borate and Tris buffer. Each buffer was produced with a range of different pH values: 8.0, 8.5, 9.0, 9.5 and 10.0. Each buffer also contained glycerol, ethanol, arginine, methionine and polysorbate. EnAd was suspended in each buffer and the formulations were stored at 4° C. Samples from each formulation were taken at regular intervals and the stability of the adenoviruses in each formulation determined by measuring the concentration of viral DNA in the sample using HPLC. A lower concentration of DNA was strong indicative of higher levels of viral degradation and hence lower stability.

The results of the experiment are shown in FIG. 1. As can be seen from FIG. 1, panel A, the pH has a significant effect on the stability of the adenoviruses. Peak stability was observed at pH 9.0 and this dropped noticeably when pH was dropped to 8.0 or raised to 10.0. A similar effect was also observed for short term (up to 8 weeks) storage at 25° C. (FIG. 1, panel B). Importantly, although there are slight variances in stability between the different buffers, the influence of pH was far more important, and the formulations which deviated the furthest from the 9.0 pH had the lowest stability regardless of which buffer was used in the formulation. The results therefore suggest that a pH of between 8.5 to 9.5 provides the best stability.

Example 2—Testing Influence of Glycerol on Stability of Adenoviral Formulations A series of experiments were conducted to determine the effect on the stability of group B adenoviral formulations when glycerol was included in the formulations. Glycerol was screened in combination using a Definitive Screening Design (DSD) at three concentrations: 9%, 14% and 20%. The results were analysed using SAS JMP statistical software. A model was created based on the DSD data. Each formulation also contained 10 mM HEPES. The adenoviruses were suspended in each formulation and the formulations were stored at 4° C. for a period of 17 weeks. The stability of the formulations was assessed at 0 weeks, 7 weeks and 17 weeks by measuring viral DNA concentration in samples using HPLC.

The results are shown in FIG. 2, panel A. As can be seen, there is a clear correlation between glycerol concentration and stability, with the formulations having higher glycerol concentrations having higher stability. The effect appears to taper off around the 17-20% glycerol concentration mark, suggesting that going beyond 20% glycerol is unlikely to produce a significant impact on stability. These results therefore suggest that a glycerol concentration of between 15-20% will significantly enhance stability and that a concentration of about 19 to 20% will likely produce the best results.

FIG. 2, panels B and C show the results of additional studies wherein 0%, 10% and 20% glycerol formulations were assessed after storage at 37° C. (FIG. 2, panel B) and storage at 25° C. FIG. 2, panel B shows that the polydispersity (which is a measure of the distribution of molecular mass within a solution—higher polydispersity correlates with higher degradation of the group B adenoviruses) was significantly higher when glycerol was excluded from the formulation compared to when 10% or 20% glycerol was added. FIG. 2, panel C shows the % change in group B adenovirus concentration over time and clearly shows a steeper and more drastic decline in concentration levels when no glycerol is used compared to when 10% or 20% glycerol was added to the formulations. Hence, these results also corroborate the findings in FIG. 2, panel A, i.e. that the inclusion of glycerol to the formulations has a significant effect on stability.

Example 3—Testing Effect of Addition of Ethanol/Arginine/Methionine/Polysorbate on Stability of Group B Adenoviral Formulations A series of experiments were conducted to determine the effect on the stability of group B adenoviral formulations when ethanol/arginine/methionine/polysorbate was omitted from the formulations. A range of different buffers were tested: HEPES 5 mM, meglumine 10 mM, TRIS 10 mM and Gly-NaCl 10 mM. None of the formulations contained any ethanol, arginine, methionine or polysorbate. The group B adenoviruses were suspended in each formulation and the formulations were stored at 4° C. for a period of 9 months. The stability and potency of the formulations were respectively assessed by HPLC and by MTS (a cell viability assay, which assesses the ability of the adenoviruses to lyse cells) at 3 month intervals, i.e. at 0 months, 3 months, 6 months and 9 months.

FIG. 3, panel A shows the potency of the group B adenoviruses over the 9 month storage period. As can be seen, there is significant degradation of the group B adenoviruses over this time frame, with the majority of the formulations approaching 0 U/vp potency by the 9 month mark. A notable exception is the meglumine containing formulation, but even this formulation was not spared from a significant drop to about 0.5 U/vp from the original starting level of 1 U/vp, i.e. the potency of the group B adenoviruses in the formulation was halved after 9 months. This result suggests that the meglumine buffer was the best at preserving the potency of the group B adenoviruses and also highlights the importance of including ethanol, arginine, methionine and polysorbate in the formulations.

FIG. 3, panel B shows the concentration levels of the group B adenoviruses over the 9 month period and again shows a trend wherein there is a significant decrease in concentration over the 9 month period for all the formulations tested. For comparison, FIG. 3, panel C shows the concentration of the group B adenoviruses a in formulation which contains ethanol/arginine/methionine/polysorbate. Note the stable group B adenovirus concentrations observed even after 20 months of storage at 4° C. Based on FIG. 3, panel B, at least with respect to concentration levels, it appears that the TRIS buffer performed the best. This experiment also shows that these components are important for overall stability of the formulations.

Example 4—Testing Individual Impact of Ethanol, Arginine and Methionine on Stability of Adenoviral Formulations Following the results of Example 3, further experiments were conducted in an attempt to determine the relative impact of each of ethanol, arginine and methionine on the stability of the group B adenovirus formulations during long term storage (24 months) at 4° C.

The results of the MTS assays are shown in FIG. 4. Three different formulations were tested, the first which included 1% ethanol (FIG. 4, panel A), the second which included 1% ethanol and 0.15 mM methionine (FIG. 4, panel C) and the third which included 1% ethanol, 0.15 mM methionine and 10 mM arginine (FIG. 4, panel B). All the formulations tested contained 5 mM HEPES, 17% glycerol and were at pH 8.0.

The results suggest that the potency of the group B adenoviruses is preserved by all 3 components in comparison with a control formulation which only had HEPES and glycerol and did not contain any of these components. The potency of the control formulation dropped to 0.5 U/vp within 3 months, whereas FIG. 4, panels A to C suggest that the period of stability is significantly extended when the 3 components are added. Specifically, the results suggest that the addition of ethanol extends the stability of the formulation by about 6 months, the addition of ethanol and methionine improves stability by about 15 months and the addition of ethanol, methionine and arginine improves stability by about 12 months. Accordingly, these results indicate that ethanol, methionine and arginine all contribute to stability. FIG. 4, panel D shows the adenovirus concentration levels as determined by HPLC and suggests that the virus concentration remains approximately constant for all 3 formulations throughout the 24 months storage period. This perhaps suggests that ethanol has the biggest impact given that ethanol is present in all 3 formulations.

Example 5—Testing Effect of Polysorbate on Stability of Group B Adenoviral Formulations This example describes the results of an experiment to assess the importance of polysorbate on adenoviral formulation stability during long term storage (20 months) at 4° C. Two formulations were tested, one with 0.115% polysorbate 80 and the other with 0.15% polysorbate 80. Both formulations also contained 20% glycerol, 5 mM HEPES, 1.5% ethanol, 10 mM arginine, 0.2 mM methionine and were at pH 8.0.

Figure 5:
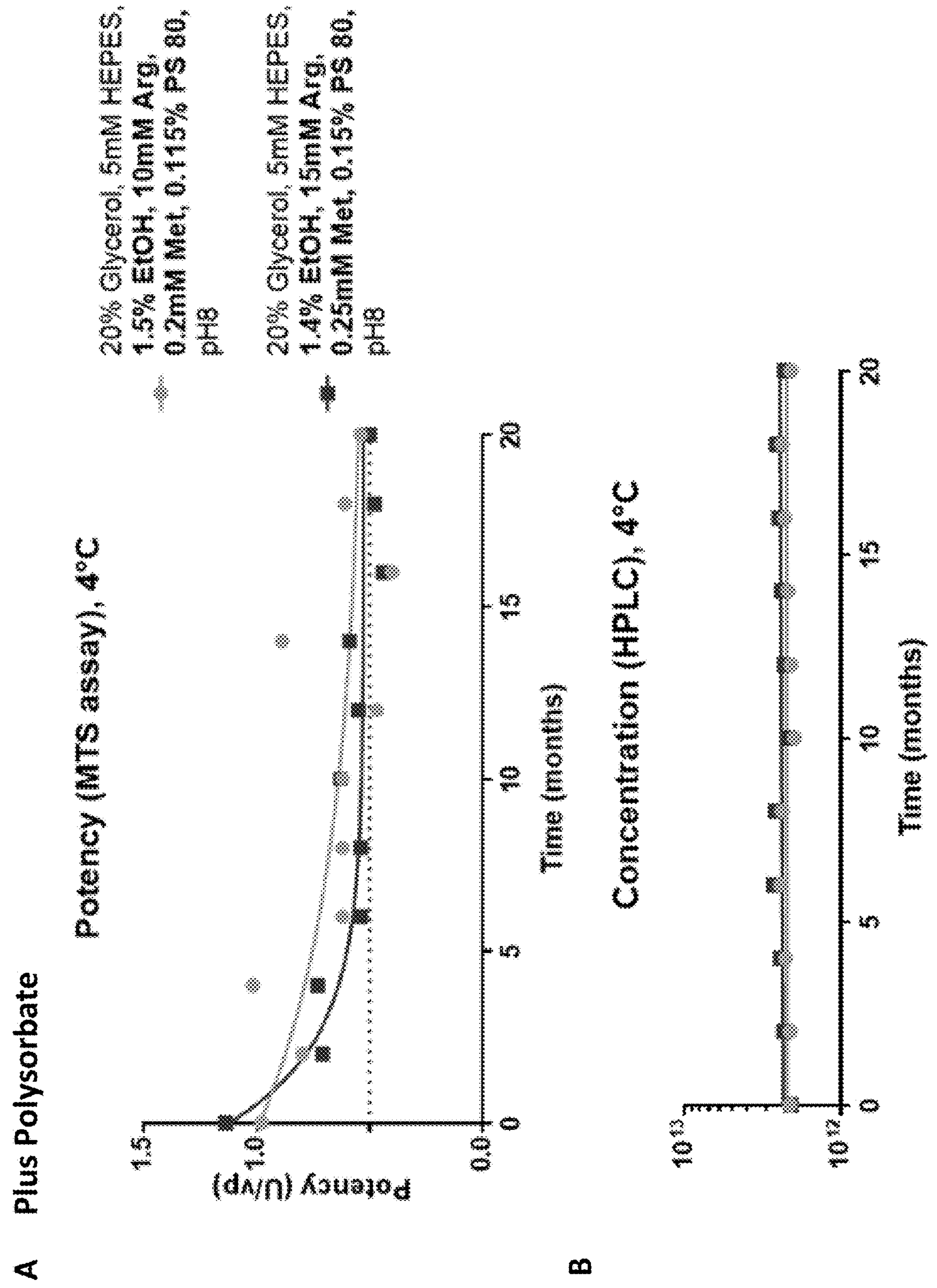
FIG. 5 shows results of experiments to assess effect of polysorbate on stability of adenoviruses. (A) graph showing potency of adenoviruses over time when 0.115% polysorbate is included in formulation vs 0.15% polysorbate. (B) graph showing concentration of adenoviruses over time when 0.115% polysorbate is included in formulation vs 0.15% polysorbate.

The results of the experiment are shown in FIG. 5. FIG. 5, panel A shows that the potency of the formulations gradually drops to about 0.5 U/vp around the 10 months mark for the formulation containing 0.15% polysorbate but then remains stable at 0.5 U/vp all the way to the 20 month point. Hence, polysorbate appears to make a significant contribution to preserving adenoviral potency in the formulations. The drop in potency is similar for the formulation containing 0.115%. This suggests that keeping the polysorbate around 0.1% results in a formulation with good stability. FIG. 5, panel B shows the adenovirus concentration levels as determined by HPLC and suggests that the virus concentration remains fairly constant for both formulations throughout the 20 months storage period.

Example 6—Testing Different Buffers and Their Impact on Stability of Group B Adenoviral Formulations This example describes the results of an experiment to compare the stability of different buffers when used in the group B adenoviral formulations during short term storage (11 weeks) at 25° C. 7 different formulations were tested: Gly-NaCl at pH 9.0, TRIS at pH 8.0, TRIS at pH 8.8, meglumine at pH 8.0, meglumine at pH 8.5, meglumine at pH 9.0 and HEPES at pH 8.0. All of the formulations contained 20% glycerol, 1.4% ethanol, 15 mM arginine, 0.15 or 0.25 mM methionine, 0.15% polysorbate.

Figure 6A:
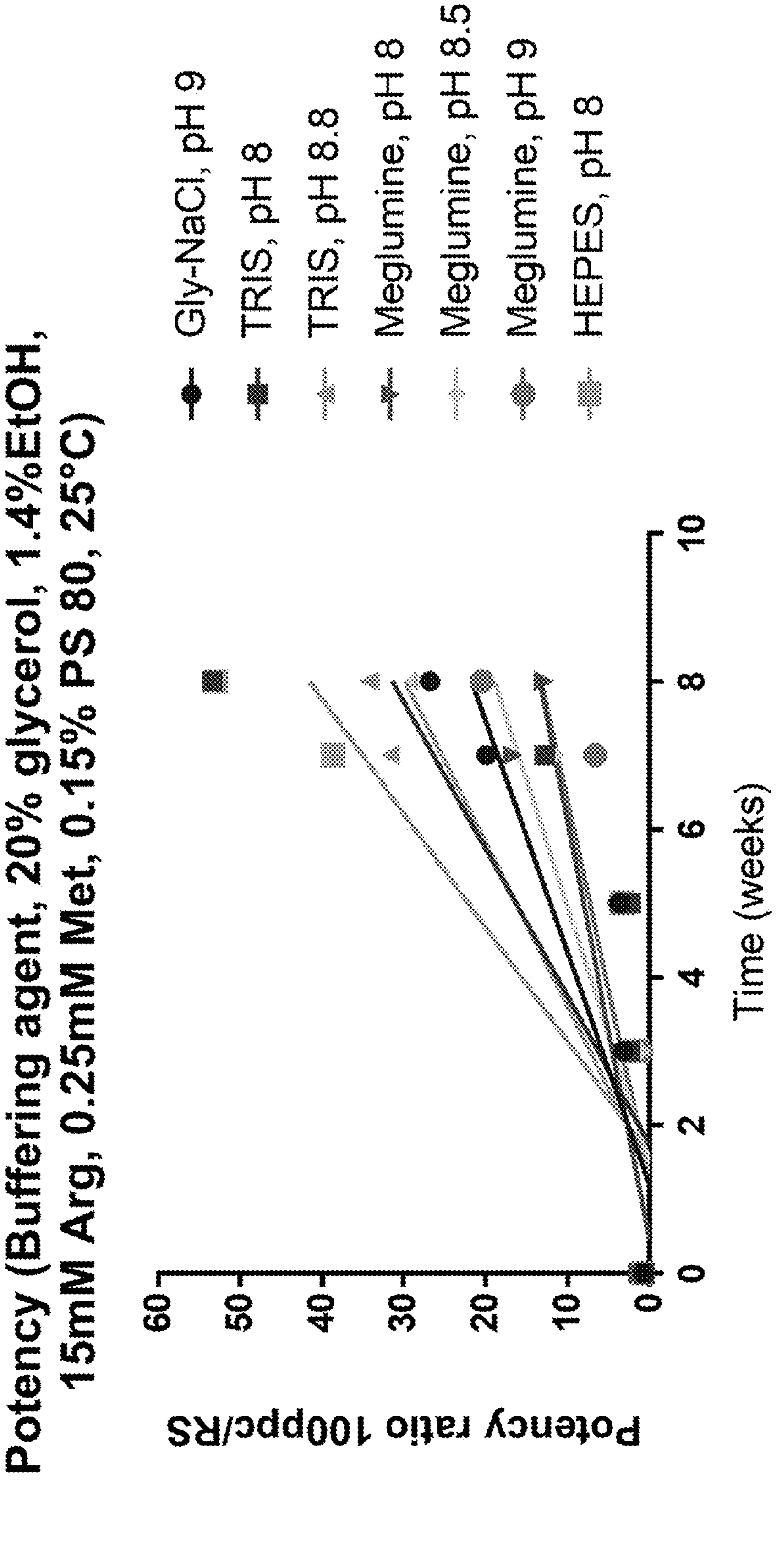
FIGS. 6A and 6B show the results of experiments to assess the stability of adenoviruses stored in different formulations at 25° C. over a 10 week time frame. (6A) potency of adenoviruses stored in different formulations over a 10 week time frame at 25° C. (6B) concentration of adenoviruses stored in different formulations over a 10 week time frame at 25° C.
Figure 6B:
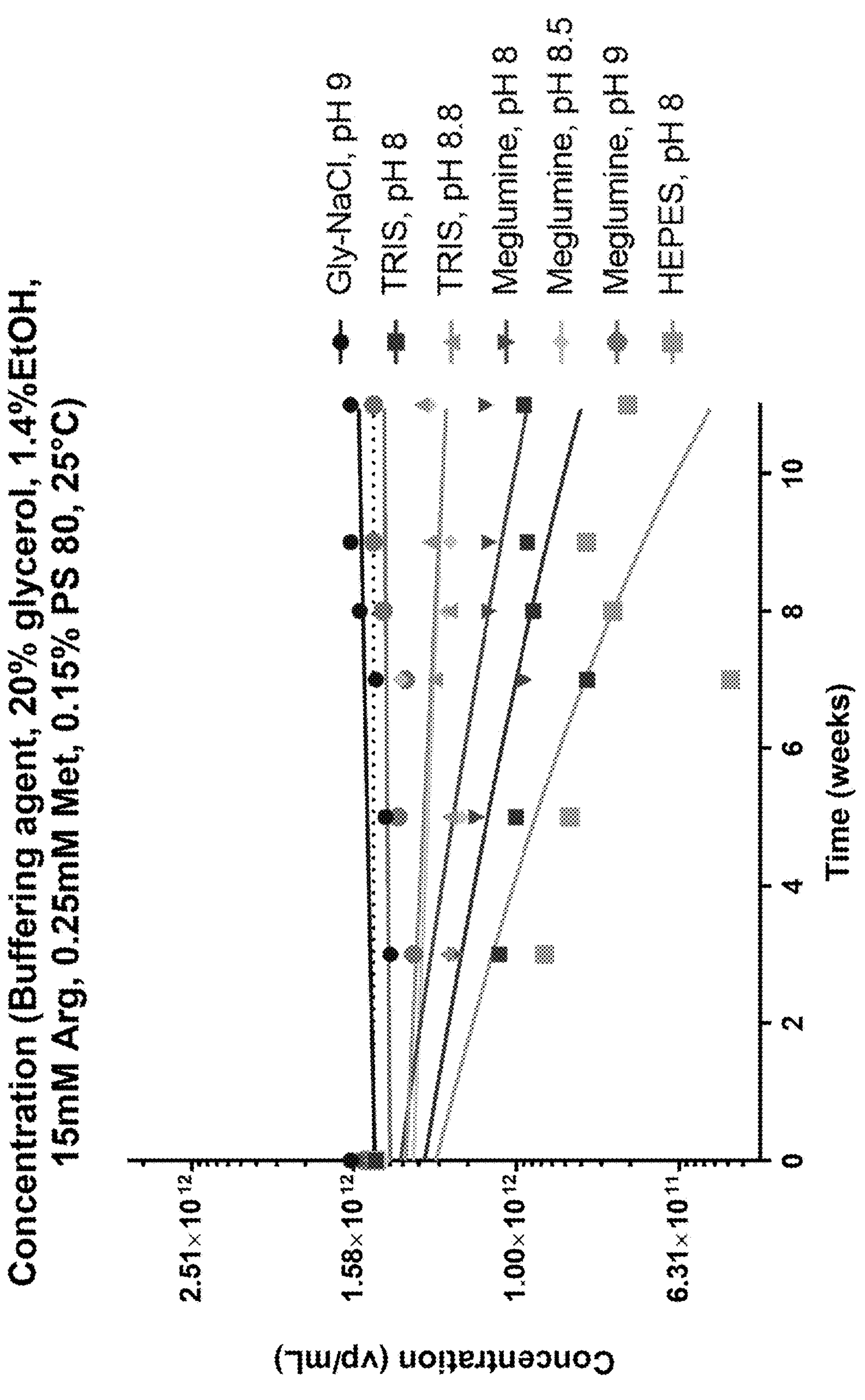

The results are shown in FIGS. 6A and 6B. FIG. 6A shows the potency ratio (100 ppc/RS) over time whilst FIG. 6B shows the concentration (vp/ml) of the formulations measured over time. Based on the graphs, an approximate order of increasing stability of the formulations appears to be HEPEs, TRIS, Gly-NaCl and meglumine (best).

Example 7

An experiment was conducted to confirm that the conditions identified using the screening methods in accelerated conditions translated to 4° C. long term storage, with a wider panel of stability indicating methods. A range of different buffers were tested all at 10 mM: Meglumine pH 8.0, Meglumine pH 8.5, Meglumine pH 9.0, TRIS pH 8.5 and Gly-NaCl. All the formulations contained 20% glycerol, 1.4% ethanol, 15 mM arginine, 0.25 mM methionine. The group B adenovirus formulations were stored at both 4° C. and −80° C. for a period of 12 months. The stability and potency of the formulations stored at 4° C. were assessed by AEX-HPLC (virus concentration), MTS (a cell viability assay, which assess the ability of adenovirus to lyse cells) and infectivity assay (assess the ability of adenovirus to infect cells and commence replication) at regular intervals. After 12 months the samples stored at −80° C. and 4° C. were analysed together using the same methods.

Figure 8A:
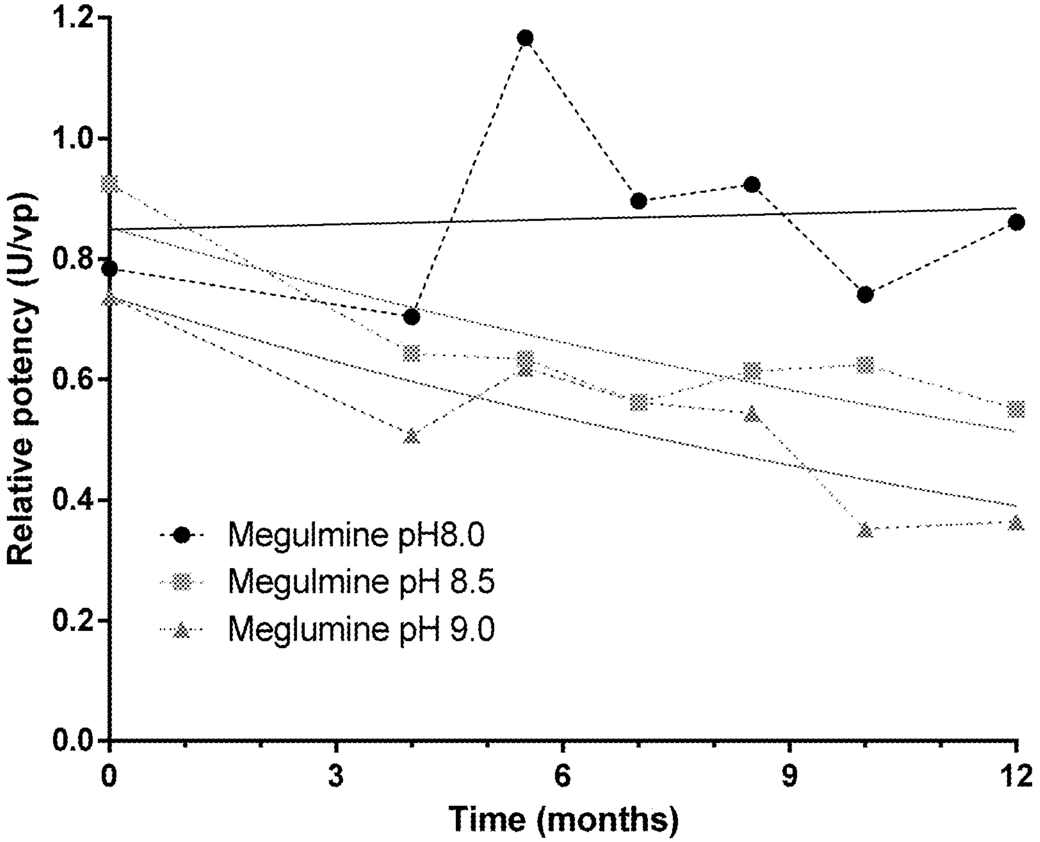
FIG. 8A shows oncolytic relative potency analysis (20% glycerol, 1.4% ethanol, 15 mM arginine, 0.25 mM methionine) stored at 4° C.
Figure 8B:
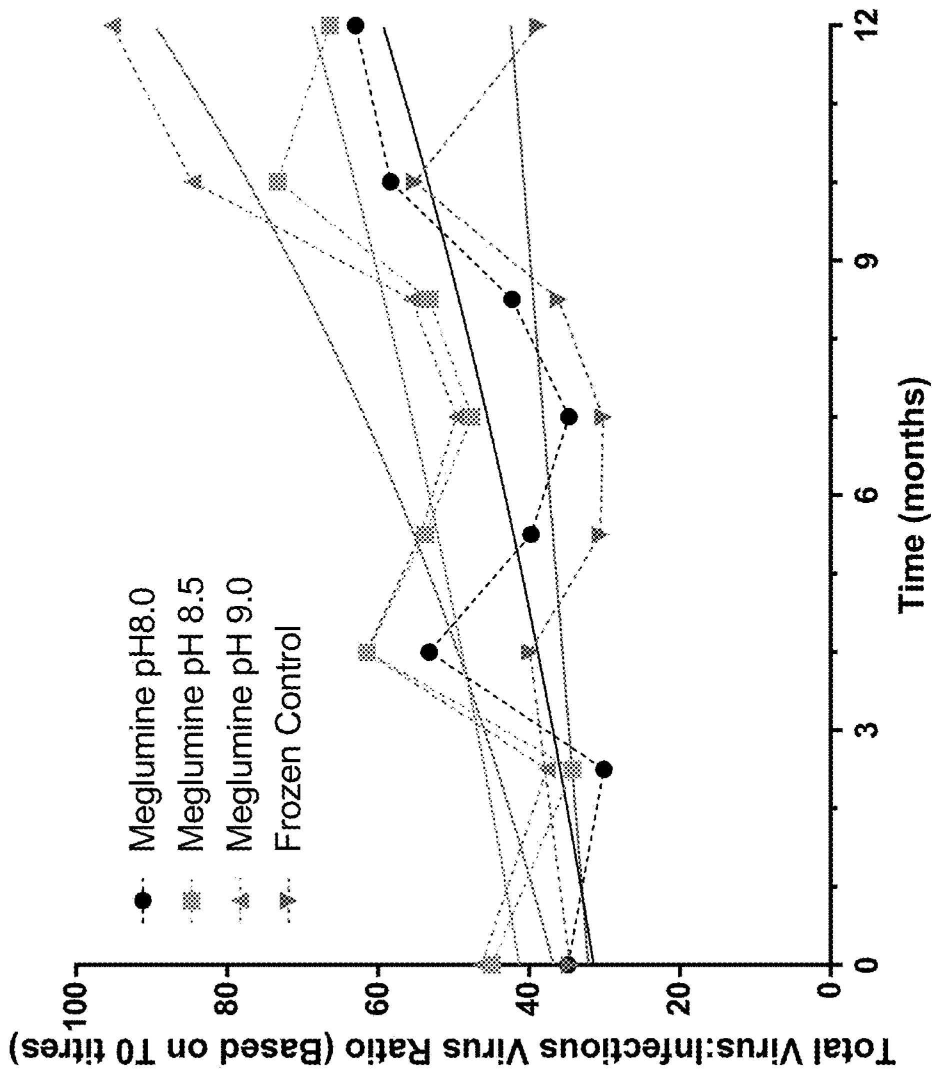
FIG. 8B shows the ratio of total virus: infectious virus particles (20% glycerol, 1.4% ethanol, 15 mM arginine, 0.25 mM methionine) stored at 4° C.

Results of the periodic analysis of the adenovirus stored at 4° C. is shown in FIGS. 8A and 8B. The MTS (relative oncolytic potency) in FIG. 8A shows that adenovirus stored in pH 8.0 is more stable for longer than when stored in pH 8.5 and pH 9.0 buffers. This is confirmed by alternative analysis as shown in FIG. 8B; the ratio of non-infectious particles present upon storage at 4° C. increases earlier as the pH rises. At pH 8.0, with the presence of the excipients (glycerol, methionine, arginine and ethanol), the adenovirus is most stable during storage.

Figure 8E:
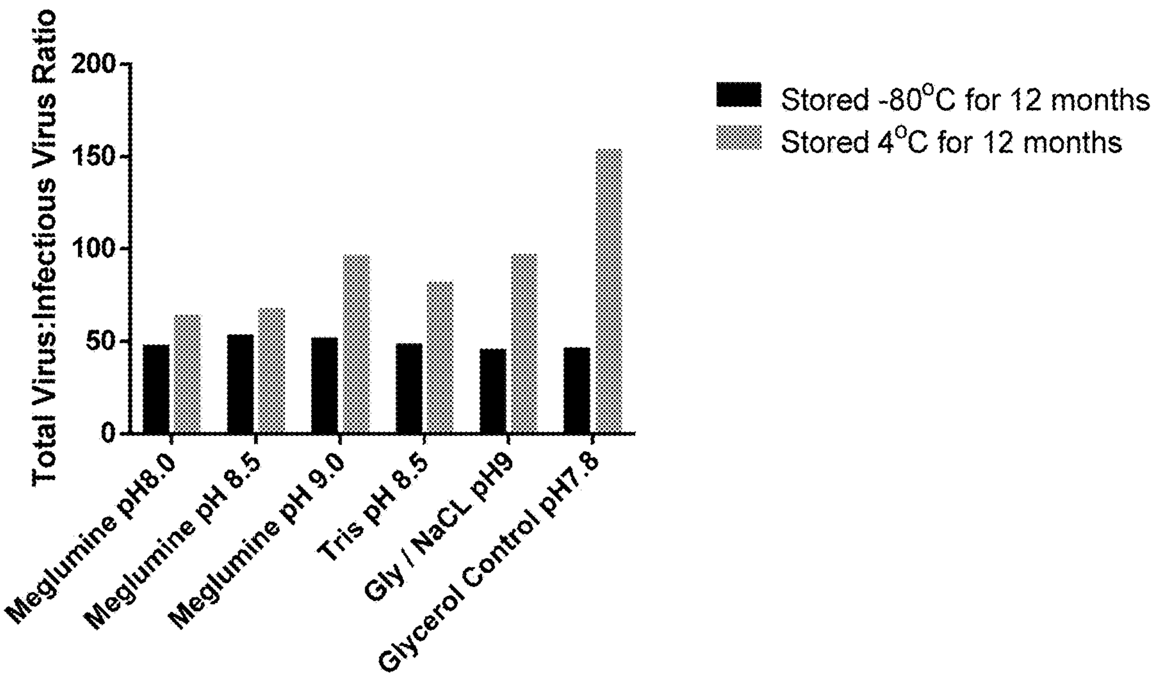
FIG. 8E shows ratio of total virus: infectious virus particle (20% glycerol, 1.4% ethanol, 15 mM arginine, 0.25 mM methionine)

FIGS. 8C, 8D and 8E compare adenovirus that has been stored at 4° C. with adenovirus stored at −80° C. for the same time period. In all Figures the glycerol control is buffered at pH 7.8 and contains 20% glycerol and no other excipients. FIG. 8D confirms that there is no change in the concentration of adenovirus as detected by AEX-HPLC in any of the tested formulations at either temperature. FIG. 8C compares the relative oncolytic potency (MTS) of adenovirus stored in both temperature conditions. The presence of one or more of the excipients (ethanol, arginine or methionine) stabilised the potency of the adenovirus when stored at 4° C. compared to −80° C. With all excipients present, the adenovirus stability as measured by potency, at 4° C. was greatest at pH 8.0, with stability decreasing as pH increased. The results in FIG. 8E, which compare the rate of formation of non-infectious particles on storage, confirms the oncolytic potency (MTS) result. Storing the virus at 4° C. for 12 months confirmed that the presence of one or more of the excipients (methionine, arginine, ethanol and glycerol) improved the stability of the adenovirus. The results also confirmed that maintenance of pH was essential for adenoviral stability when stored at 4° C. In this experiment the optimal pH for stability was 8.0 and stability decreased with an increase in pH. In example 1, the data indicated that pH >8.0 would be more stable, with an optimum at 8.5-9.0. However, the only buffer condition tested at pH 8.0 was HEPES. It can therefore be concluded that Meglumine, a sugar-based buffering agent has greater stabilising effect on the adenovirus at pH 8.0 compared to the HEPES buffer used in example 1.

SEQUENCE LISTING

The patent contains a lengthy sequence listing. A copy of the sequence listing is available in electronic form from the USPTO web site (https://seqdata.uspto.gov/docdetail?docId=US12691150B2). An electronic copy of the sequence listing will also be available from the USPTO upon request and payment of the fee set forth in 37 CFR 1.19(b)(3).

The invention claimed is:

1. A liquid formulation suitable for a group B adenovirus, comprising:

a) a group B adenovirus;

b) 15 to 25% v/v glycerol;

c) methionine or arginine; and d) buffer, wherein the pH of the formulation is in the range of 8.0 to 9.6 and wherein the formulation does not comprise a divalent cation.

2. The formulation of claim 1, wherein the formulation does not comprise a sugar.

3. The formulation of claim 1, wherein the formulation is for intravenous administration.

4. The formulation of claim 3, wherein the formulation is for administration by slow injection or by infusion.

5. The formulation of claim 1, wherein the formulation further comprises a surfactant.

6. The formulation of claim 5, wherein the surfactant is polysorbate, optionally wherein the polysorbate is polysorbate 80.

7. The formulation of claim 6, wherein the formulation comprises 0.05-0.15% polysorbate.

8. The formulation of claim 1, wherein the formulation comprises 0.01-0.3 mM methionine.

9. The formulation of claim 1, wherein the formulation comprises 5-20 mM arginine.

10. The formulation of claim 1, wherein the buffer is selected from meglumine, glycine, TRIS, and combinations thereof.

11. The formulation of claim 1, wherein the formulation does not comprise HEPES buffer.

12. The formulation of claim 1, wherein the formulation comprises:

a) 15 to 20% v/v glycerol;

b) 1 to 1.5% v/v ethanol;

c) 0.1 to 0.2% v/v polysorbate 80;

d) 0.2 to 0.3 mM methionine; and e) 10 to 20 mM arginine.

13. The formulation of claim 1, wherein the group B adenovirus is replication competent.

14. The formulation of claim 1, wherein the group B adenovirus is Ad11 or Enadenotucirev (EnAd).

15. The formulation of claim 1, wherein the formulation further comprises 0.1 to 1.5% v/v ethanol.

* * * * *